United States Patent
Barnham et al.

(10) Patent No.: US 7,704,987 B1
(45) Date of Patent: Apr. 27, 2010

(54) β-AMYLOID PEPTIDE INHIBITORS

(75) Inventors: Kevin Jeffrey Barnham, West Brunswick (AU); Thomas David McCarthy, Malvern East (AU); Susanne Pallich, Deer Park (AU); Barry Ross Matthews, Olinda (AU); Robert Alan Cherny, Brighton East (AU)

(73) Assignee: Prana Biotechnology Ltd (AU)

( * ) Notice: Subject to any disclaimer, the term of this patent is extended or adjusted under 35 U.S.C. 154(b) by 587 days.

(21) Appl. No.: 10/031,478

(22) PCT Filed: Jul. 21, 2000

(86) PCT No.: PCT/AU00/00886

§ 371 (c)(1), (2), (4) Date: Jul. 29, 2002

(87) PCT Pub. No.: WO01/07442

PCT Pub. Date: Feb. 1, 2001

(30) Foreign Application Priority Data

Jul. 23, 1999 (AU) .................................. PQ1804

(51) Int. Cl.
A61K 31/555 (2006.01)
A61K 31/4745 (2006.01)
C07D 471/14 (2006.01)

(52) U.S. Cl. .............................. 514/185; 546/88
(58) Field of Classification Search .................... None
See application file for complete search history.

(56) References Cited

U.S. PATENT DOCUMENTS

| 4,813,399 | A | * | 3/1989 | Gordon | 600/12 |
|---|---|---|---|---|---|
| 5,004,697 | A | * | 4/1991 | Pardridge | 424/1.49 |
| 5,696,109 | A | | 12/1997 | Malfroy-Camine et al. | 514/185 |
| 5,817,626 | A | * | 10/1998 | Findeis et al. | 514/12 |
| 5,854,204 | A | * | 12/1998 | Findeis et al. | 514/2 |
| 5,854,215 | A | * | 12/1998 | Findeis et al. | 514/12 |
| 5,958,883 | A | | 9/1999 | Snow | 514/16 |
| 5,994,339 | A | * | 11/1999 | Crapo et al. | 514/185 |
| 6,054,114 | A | * | 4/2000 | Lansbury et al. | 424/1.11 |
| 6,177,419 | B1 | | 1/2001 | Campbell et al. | 514/183 |
| 6,303,567 | B1 | * | 10/2001 | Findeis et al. | 514/2 |
| 6,319,498 | B1 | * | 11/2001 | Findeis et al. | 424/94.3 |
| 6,323,218 | B1 | * | 11/2001 | Bush et al. | 514/311 |

FOREIGN PATENT DOCUMENTS

| WO | WO 95/12815 | | 5/1995 |
|---|---|---|---|
| WO | WO 9628471 A1 | * | 9/1996 |
| WO | WO 9640148 A1 | * | 12/1996 |
| WO | WO 97/21431 | | 6/1997 |
| WO | WO 9741856 A1 | * | 11/1997 |
| WO | WO 98/12815 | | 3/1998 |
| WO | WO 98/44955 | | 10/1998 |
| WO | WO 99/34807 | | 7/1999 |
| WO | WO 00/09111 | | 2/2000 |

OTHER PUBLICATIONS

H Shao, et al. J. Mol. Biol. (1999) 285, 755-773.*
T. Nordenberg. "It's Quitin' Time: Smokers Need Not Rely on Willpower Alone." FDA Publication 99-1288, May 1999, 6 pages.*
ADEAR Alzheimer's Disease Medications fact sheet. NIH Publication 03-3431. Alzheimer's Disease Education & Referral Center. National Institute on Aging, NIH, US Dept HHS. Jul. 2004. 6 pages.*
C Ballard, et al. Quetiapine and rivastigmine and cognitive decline in Alzheimer's disease : randomized double blind placebo controlled trial. British Medical Journal. Feb. 18, 2005, 5 pages.*
WebMD Alzheimer's Disease: treatment overview. Web document <http://my.webmd.com/content/article/71/81399.htm> Accessed Feb. 22, 2005. 2 pages.*
C. Soto, et al. Inhibition of Alzheimer's Amyloidosis by Peptides That Prevent β-Sheet Conformation. Biochem. Biophys. Res. Comm. (1996) 226(3), pp. 672-680.*
M.A. Findeis, et al. Modified-Peptide Inhibitors of Amyloid β-Peptide Polymerization. Biochemistry (1999) 38(21), pp. 6791-6800.*
E.T. Sutton, et al. β-Amyloid-induced Endothelial Necrosis and Inhibtion of Nitric Oxide Production. Exp. Cell Res. (1997) 230, pp. 368-376.*
D.E. Brenner et al. Neurology (1993) 43, pp. 293-300.*
E. Hellström-Lindahl et al. Br. J. Neurosci. (2004) 19, pp. 2903-2910.*
M.D. Li et al. J. Neurosci. (2000) 15, pp. 1318-1323.*
S. Everts, "Brain Barricade". C& E News (2007), 85(23), pp. 33-36.*
Saito, et al. PNAS (1995) 92, pp. 10227-10231.*
E.M. Prokopchuk et al. Organometallics. (1999) 18(15), pp. 2861-2866.*
A.J. Canty et al. Organometallics. (1999) 18(14), pp. 2660-2667.*
W.B. Connick et al. Inorg. Chem. (1999) 38(14), pp. 3264-3265.*
Miura et al., "Metal Binding Modes of Alzheimer's Amyloid-B-peptide in Insoluble Aggregates and Soluble Complexes," Biochemistry, vol. 39, 2000, pp. 7024-7031.
Atwood et al., "Dramatic Aggregation of Alzheimer AB by Cu(II) is Induced by Conditions Representing Physiological Acidosis," Journal of Biological Chemistry, vol. 273, No. 21, 1998, pp. 12817-12826.

(Continued)

Primary Examiner—Andrew D Kosar
(74) Attorney, Agent, or Firm—Scully, Scott, Murphy & Presser, P.C.

(57) ABSTRACT

The present invention relates to compounds which inhibit the binding of metal ions to a region in the N-terminal loop of the β-amyloid peptide which includes a cluster of histidine residues. In addition, the invention relates to pharmaceutical compositions including these compounds as the active agent, and to methods of treatment involving the administration of these compounds. The compounds of the invention are useful in the treatment of Alzheimer's Disease and other amyloid-related conditions. In a first aspect the present invention provides a compound which interacts with the β-amyloid peptide in such a way that the N-terminal loop of the peptide (amino acid residues 1-15) is blocked or destabilised, thereby inhibiting the binding of one or more metal ions to at least one histidine residue within the N-terminal loop. Preferably the compound inhibits binding of $Cu^{2+}$, $Zn^{2+}$ and $Fe^{3+}$ ions, but not $Mg^{2+}$ or $Ca^{2+}$ ions.

19 Claims, 9 Drawing Sheets

OTHER PUBLICATIONS

Bartolotti et al., "A Model for the Tertiary Structure of the B-amyloid Peptide," Alzheimer's Research 2, vol. 2, 1996, pp. 189-194.

Chemical Abstract: Chan et al., "Structural and Mechanistic Studies of Coordination Compounds," J. Chem. Soc., Dalton Transactions, 1976, No. 10. pp. 858-862.

Shao et al., "Solution Structures of Micelle-bound Amyloid B-(1-40) and B-(1-42) Peptides of Alzheimer's Disease," Journal of Molecular Biology, vol. 285, Jan. 1999, pp. 755-773.

Frenkel et al., "High Affinity Binding of Monoclonal Antibodies of the Sequential Epitope EFRH of B-amyloid Peptide is Essential for Modulation of Fibrillar Aggregation," Journal of Neuroimmunology, vol. 95, Mar. 1999, pp. 136-142.

Pappolla et al., "Inhibition of Alzheimer B-fibrillogenesis by Melatonin," Journal of Biological Chemistry, vol. 273, No. 13, 1998 pp. 7185-7188.

Talafous et al, "Solution Structure of Residues 1-28 of the Amyloid B-peptide," Biochemistry, vol. 33, 1994, pp. 7788-7796.

Giulian et al., "The HHQK Domain of B-amyloid Provides a Structural Basis for the Immunopathology of Alzheimer's Disease," vol. 273. No. 45, 1998, pp. 29719-29726.

Caughey, W. S. et al., "Inhibition of protease-resistant prion protein formation by porphyrins and phthalocyanines", *Proc. Natl. Acad. Sci. USA*, 95: 12117-12122 (1998), XP000904870.

Liu, Su-Ting et al., "Histidine-13 Is a Crucial Residue in the Zinc Ion-Induced Aggregation of the Aβ Peptide of Alzheimer's Disease", *Biochemistry*, 38(29): 9373-9378 (1999), XP002266540.

Howlett, D. et al., "Hemin and related porphyrins inhibit β-amyloid aggregation", *FEBS Letters*, 417: 249-251 (1997), XP000891946.

Gray, D. N. et al., "Resolubilization of Alzheimer and APP transgenic beta amyloid plaque by copper chelators", 28$^{th}$ Annual Meeting of the Society for Neuroscience, Part 1, Nov. 7-12, 1998, Society for Neuroscience, Abstract, No. 282.13.

Cherny, R. A. et al., "Aqueous Dissolution of Alzheimer's Disease Aβ Amyloid Deposits by Biometal Depletion", *The Journal of Biological Chemistry*, 274(33): 23223-23228 (1999).

* cited by examiner

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: synthetic peptide

<400> SEQUENCE: 1

Lys Leu Val Phe Phe Ala
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic peptide

<400> SEQUENCE: 2

Leu Val Phe Phe Ala
1               5
```

β-AMYLOID PEPTIDE INHIBITORS

The present invention relates to compounds which inhibit the binding of metal ions to the N-terminal region of the β-amyloid peptide. In addition, the present invention relates to pharmaceutical compositions including these compounds as the active agent, and to methods of treatment involving the administration of these compounds. The compounds of the invention are useful in the treatment of Alzheimer's disease.

BACKGROUND OF THE INVENTION

Alzheimer's disease (AD) is characterised by the presence of distinctive lesions in the victim's brain. These brain lesions include abnormal intracellular filaments called neurofibrillary tangles, and extracellular deposits of amyloid in senile, or amyloid, plaques. Amyloid deposits are also present in the walls of cerebral blood vessels of Alzheimer's patients.

The major constituent of amyloid plaques has been identified as a 4 kilodalton peptide (39-43 residues) called β-amyloid peptide (Aβ) (Glenner and Wong, 1984). Diffuse deposits of Aβ peptides are frequently observed in normal adult brains, whereas Alzheimer's disease brain tissue is characterised by more compacted, dense-core β-amyloid plaques. These observations suggest that Aβ deposition precedes, and contributes to, the destruction of neurons that occurs in Alzheimer's disease. In further support of a direct pathogenic role for AD, β-amyloid has been shown to be toxic to mature neurons both in culture and in vivo (Yanker et al., 1989).

Natural Aβ is derived from proteolysis from a much longer protein known as the amyloid precursor protein (APP) (Kang, J et al, 1987). The APP gene maps to chromosome 21, thereby providing an explanation for the β-amyloid deposition seen at an early age in individuals with Down's syndrome, which is caused by trisomy of chromosome 21.

Aβ peptides are cleaved from APP, and then undergo aggregation to produce the insoluble toxic β-sheet structures which are found in extracellular deposits in Alzheimer's disease and Down's syndrome. Recent data suggest that the aggregated peptide has redox properties and can generate reactive oxygen species, which attack enzymes and possibly cell membranes, causing neurotoxicity (Markesbery, W. R. 1997). Antioxidants are known to protect against Aβ-induced toxicity.

Aβ has been shown to bind copper and iron in stoichiometric amounts, with the associated formation of reactive oxygen species such as peroxides and hydroxide radicals, which are possible sources of the neurotoxicity (Bush et al., 1998). While the formation of peroxide in post-mortem samples of Alzheimer's disease brain has been observed, there was little peroxide formation in control tissue (Cherny et al., 1998). The peroxidase activity observed in the samples of Alzheimer's disease brain was abolished when treated with certain chelators (Cherny et al., 1998). The formation of reactive oxygen species was accompanied by a reduction in the valence state of the metal, ie Cu(II) to Cu(I) and Fe(III) to Fe(II) (Atwood et al., 1998a). Reactive oxygen species can also lead to free radical formation on the Aβ peptide, which leads over time to covalent cross-linking of the Aβ peptides (Bush et al., 1998). In addition, a number of metal ions, including Zn, Ni and Cu, have been shown to induce aggregation of Aβ (Atwood et al., 1998b). When brain tissue from both control and Alzheimer's disease-affected subjects was treated with chelators which are specific for zinc and copper, there was greatly enhanced solubilisation of Aβ, with an increase of up to 700%, suggesting that zinc and copper play a role in the assembly of the Aβ deposits (Cherny et al., 1998).

Histidine residues have been implicated in the binding of metal ions to Aβ peptides. For instance rat Aβ1-40, in which His13 is mutated to Arg, does not aggregate, nor does Aβ1-40 treated with diethyl pyrocarbonate, which binds to the imidazole nitrogen of histidine (Atwood et al., 1998). Subsequently to the priority date of this application, it was reported that three histidine residues in the N-terminal hydrophilic region of human Aβ provide primary metal binding sites, and that the solubility of the complex between metal and Aβ depends on the mode of metal binding. The authors proposed that $Cu^{2+}$ would protect Aβ against Zn-induced aggregation by competing with zinc ions for binding sites on the histidine residues (Miura et al., 2000).

In contrast, we propose that inhibition of binding of zinc, copper and/or iron to the Aβ peptide will have significant therapeutic value in the treatment of Alzheimer's disease.

It has been reported that certain tetrapyrroles, especially certain porphyrin and phthalocyanine compounds inhibit conversion of normal, protease-sensitive prion protein (PrPsen) to the protease-resistant form (PrPres) which is implicated in the pathogenesis of transmissible spongiform encephalopathies (TSEs) such as Creutzfeldt-Jacob disease (Caughey et al., 1998), and that three of these compounds inhibited TSE disease in vivo (Priola et al., 2000). However, both metal-free and metal-complexed tetrapyrroles were active, and the authors considered that the mechanism of action involved direct interaction between the compound and the infectious agent. Although the authors speculated that the compounds might also be useful in the treatment of non-prion mediated amyloid-related conditions, such as Alzheimer's disease or Type II diabetes, this was no more than speculation (Priola et al., 2000). Moreover, all of the compounds disclosed have multiple substitutions or the tetrapyrrole ring, whereas the tetrapyrrole compounds of the present invention are preferably substituted only on one of the rings.

It will be clearly understood that, although a number of prior art publications are referred to herein, this reference does not constitute an admission that any of these documents forms part of the common general knowledge in the art, in Australia or in any other country.

SUMMARY OF THE INVENTION

The present inventors have now found that zinc and copper bind predominantly to a region in the N-terminal loop of Aβ which includes a cluster of histidine residues. This finding provides the basis for the rational design or selection of inhibitors of the binding of zinc, copper and/or iron to Aβ.

Accordingly, in a first aspect the present invention provides a compound which interacts with the β-amyloid peptide in such a way that the N-terminal loop of the peptide (amino acid residues 1-15) is blocked or destabilised, thereby inhibiting the binding of one or more metal ions to at least one histidine residue within the N-terminal loop.

Preferably the compound inhibits binding of $Cu^{2+}$, $Z^{2+}$ and $Fe^{3+}$ ions, but not $Mg^{2+}$ or $Ca^{2+}$ ions.

Preferably the compound has a conformation and polarity such that it binds to at least one, more preferably at least two, and more preferably three histidine residues in the N-terminal loop, selected from the group consisting of His6, His13 and His14. More preferably the compound also binds to at least one additional amino acid in the N-terminal loop, selected from the group consisting of Asp7, Tyr10, and Glu11.

The compound may have acidic groups which interact with one or more of the His residues in the N-terminal loop. For example, the compound may be represented as follows:

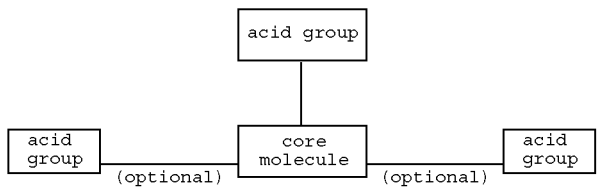

wherein the core molecule has a conformation and polarity such that the acid group(s) interact with one of more of His6, His13 and His14. The acid may be any acid group, including, but not limited to, $CO_2H$, $PO_3H_2$, $SO_3H$, $OSO_3H_2$, $OPO_3H_2$ and the like.

The compound may be a molecule with one to three carboxylic acid groups, the length of the molecule being such that it can be received within the N-terminal loop, and such that at least one carboxyl group is in proximity to at least one of the histidine residues. Without wishing to be bound by theory, we believe that it is likely that such molecules will have a molecular mass in the region of 2000 Daltons.

The compound may be an organic molecule, a peptide or a metal complex. In this aspect of the invention, however, it is preferred that the compound is not a metal complex. Preferably the compound has overall hydrophobic character. More preferably the compound is able to penetrate the blood-brain barrier.

In a particularly preferred embodiment of the invention, the inhibitor compound comprises, or is conjugated to, a targeting moiety.

The term "targeting moiety" as used herein refers to a functional group which will specifically interact with the β-amyloid peptide. That is, the inhibitor compound includes or is covalently linked to a targeting moiety which will specifically bind to or associate with the β-amyloid peptide. Suitable targeting moieties include, but are not limited to, polypeptides, nucleic acids, carbohydrates, lipids, β-amyloid ligands, antibodies, dyes and the like. In a preferred embodiment the targeting moiety has a hydrophobic region which interacts with the tail of the β-amyloid peptide. For example, the targeting moiety may include a fatty acid molecule.

Preferably the targeting moiety targets the compound to the site defined by residues 15-21 of the β-amyloid peptide. The targeting moiety may be a peptide which comprises a sequence which corresponds to that of residues 15-21 of the β-amyloid peptide. More preferably the inhibitor-targeting moiety complex is able to penetrate the blood-brain barrier.

In a second aspect, the invention provides a method of selecting or designing a compound which inhibits the binding of metal ions to the N-terminal loop of the β-amyloid peptide, which method comprises the steps of (i) selecting or designing a compound which has a conformation and polarity such that it binds to at least one, more preferably at least two and more preferably three amino acids in the N-terminal loop, selected from the group consisting of His6, His 13 and His14; and (ii) testing the compound for the ability to inhibit binding of metal ions to the N-terminal loop of the β-amyloid peptide.

Preferably the compound inhibits binding of $Cu^{2+}$, $Zn^{2+}$ and $Fe^{3+}$ ions, but not $Mg^{2+}$ or $Ca^{2+}$ ions.

Preferably the compound has a conformation or polarity such that it also binds to at least one amino acid in the N-terminal loop, selected from the group consisting of Asp7, Tyr10, and Glu11. Preferably the compound also has overall hydrophobic character. More preferably the compound is able to penetrate the blood-brain barrier.

In a third aspect, the invention provides a compound which inhibits the binding of metal ions to the N-terminal loop of the β-amyloid peptide, wherein the compound is obtained by a method according to the second aspect of the invention.

In a fourth aspect, the invention provides a composition comprising a compound according to the first or the third aspects of the present invention, together with a pharmaceutically acceptable carrier. Methods and pharmaceutical carriers for preparation of pharmaceutical compositions are well known in the art, as set out in textbooks such as Remington's Pharmaceutical Sciences, 19th Edition, Mack Publishing Company, Easton, Pa., USA.

The compounds of the present invention may be formulated into pharmaceutical compositions, and administered in therapeutically effective doses. The term "therapeutically effective dose" means a dose which results in the inhibition of natural binding of metal ions to the N-terminal loop of the β-amyloid peptide. The pharmaceutical compositions may be administered in a number of ways, including, but not limited to, orally, subcutaneously, intravenously, intraperitoneally and intranasally. The most appropriate dose and route of administration will be dependent on the age and general state of health of the subject to be treated, and will be at the discretion of the attending physician. This dose can be readily ascertained by one skilled in the art, using well-known techniques.

In a fifth aspect, the invention provides a method of inhibiting the binding of one or more metal ions to the β-amyloid peptide, or inhibiting the aggregation of β-amyloid peptide, which method comprises the step of exposing the peptide to a compound which blocks or destabilises the N-terminal loop of the peptide, thereby inhibiting the binding of one or more metal ions to at least one histidine residue within the N-terminal loop.

Preferably the compound has a conformation and polarity such that it binds to at least one, more preferably at least two, and more preferably three histidine residues in the N-terminal loop of the β-amyloid peptide, selected from the group consisting of His6, His13 and His14. More preferably the compound also binds to at least one additional amino acid in the N-terminal loop, selected from the group consisting of Asp7, Tyr10, and Glu11.

In a particularly preferred embodiment, the compound is a metal complex which can exchange or bind functional moieties such as histidine, with the proviso that the compound is not haemin or haematin. Preferably the metal complex is capable of binding between 1 and 3, preferably 2 or 3, histidine residues of the N-terminal loop of the β-amyloid peptide. The complex may bind to other residues in addition to the histidine residues. More preferably the complex also binds to at least one additional amino acid in the N-terminal loop, selected from the group consisting of Asp7, Tyr1O, and Glu11.

Metal ions capable of binding to the imidazole nitrogen(s) of histidine include Mn, Fe, Co, Ni, Cu, Zn, Ru, Pd, Ag, Cd, Pt, Au, Rh and Hg. Complexes of these metals are expected to be predominantly four coordinate tetrahedral (distorted tetrahedral)/square planar) complexes, five coordinate complexes with either a trigonal bipyramid or square pyramid configuration, or six coordinate octahedral (or distorted octahedral) complexes.

Even more preferably the inhibitor compound comprises, or is conjugated to, a targeting moiety. Preferably the targeting moiety targets the compound to the site defined by residues 15-21 on the β-amyloid peptide.

In a further preferred embodiment, the inhibition of binding of one or more metal ions to the β-amyloid peptide occurs in vivo.

In a sixth aspect, the invention provides a method of prevention, treatment or alleviation of Alzhemier's disease which method comprises the step of administering a compound or a pharmaceutical composition according to the invention to a subject in need of such treatment.

The patient is monitored for clinical improvement, which may commence within as little as one week, but more probably may be observed at six weeks, and may take as long as 12 months. The normal clinical indices which are used in the monitoring of patients with the relevant condition are used. Where the treatment is prophylactic, the patient is monitored for signs of development of the condition. The attending clinician will be aware of the most suitable tests to use.

Where this method is to be used for prophylactic purposes, the subject is preferably one at increased risk of developing the condition. For example, the subject may have one or more family members with the condition, eg. familial Alzheimer's disease, or may have trisomy of chromosome 21 (Down's syndrome).

It will be clearly understood that, for the purposes of this aspect of the invention, the compound is not haemin.

In a seventh aspect, the invention provides a method of monitoring the efficacy of treatment according to the method of the invention, comprising the steps of obtaining a sample of a biological fluid for a patient undergoing treatment, and measuring the level of Aβ in the sample, in which increased Aβ levels compared to levels of Aβ in a normal control sample are indicative of the efficacy of the treatment.

For the purposes of this specification it will be clearly understood that the word "comprising" means "including but not limited to", and that the word "comprises" has a corresponding meaning.

DETAILED DESCRIPTION OF THE INVENTION

Figure 1:
FIG. 1 is a representation of the β-amyloid peptide showing a structured turn in the region of amino acid residues 15-21.

The present inventors have developed three-dimensional structural information concerning the N-terminal region of the β-amyloid peptide, and have identified a cluster of three histidine residues which constitute a binding site for metal ions. This information provides a rational basis for the development of compounds which inhibit the binding of metal ions to the N-terminal loop of the β-amyloid peptide. Such inhibitors have the potential to inhibit aggregation of β-amyloid peptides and to reduce metal-induced neurotoxicity. Accordingly, these inhibitors are likely to have therapeutic value in the treatment of diseases such as Alzheimer's disease.

Using the structural information provided by the inventors, the general principles of drug design can be applied by persons skilled in the art to produce compounds which preferentially bind to at least one of the histidine residues in the N-terminal loop (ie His6, His13 or His14), and inhibit the binding of metal ions to the N-terminal loop of the amyloid peptide.

Preferred inhibitors within the context of the present invention include metal complexes which can exchange or bind functional moieties such as histidine. Preferably the metal complex is capable of binding between 1 and 3, preferably 2 or 3, histidine residues of the N-terminal loop of the β-amyloid peptide. The complex may bind to other residues in addition to the histidine residues. Metal ions capable of binding to the imidazole nitrogen of histidine include Mn, Fe, Co, Ni, Cu, Zn, Ru, Pd, Ag, Cd, Pt, Au, Rh and Hg. Complexes of these metals are expected to be predominantly four coordinate tetrahedral (distorted tetrahedral)/square planar complexes, or six coordinate octahedral (or distorted octahedral) complexes. In the case of the four coordinate complexes they could react with the β-amyloid peptide to replace ligands; alternatively, by binding to His residues as well as to their initial ligand(s) their coordination number is increased to 5 or 6. Five coordinate complexes with either a trigonal bipyramid or square pyramid configuration may also be used. Examples of suitable complexes are shown below.

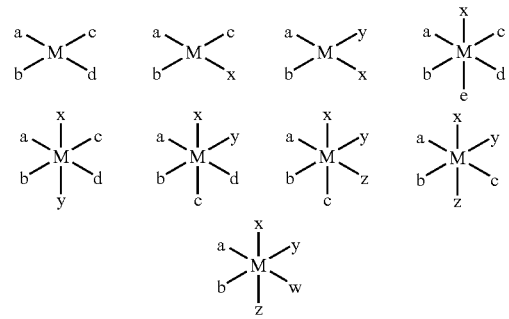

In these formulae:

(i) a, b, c, d and e are non-leaving groups, preferably chelating groups including Schiff bases, porphyrin rings, macrocycles, polyamino-carboxylates, heterocyclic aromatic groups such as 2,2' bipyridine and 1,10-phenanthrolene, peptides, nucleobases, or chelating ligands in which one of the donor atoms is a phosphine phosphorus atom;

(ii) M is a metal; and (iii) w, x, y and z are leaving groups (ie those groups which will be replaced by histidine and possibly other residues when the metal complex reacts with the β-amyloid peptide), and include halogens, amines, ammonia, pyridyls, imidazoles, nucleobases, peptides, H$_2$O/OH, carboxylic acids, phosphates, sulfates, nitrate, triflate, or alkoxides.

The term "nucleobase" means a purine or a pyrimidine, or an analogue thereof. It will be appreciated that multidentate macrocyclic ligands may have a variety of donor atoms, and that it is possible that one or more of the non-leaving groups could be a stable monodentate ligand such as cyanide, or an organic group such as a methyl group.

Those skilled in the art will recognise that the appropriate combination of non-leaving and leaving groups will be dependent on the identity of the metal.

Metal complexes which have the potential to bind to histidine residues are described in WO 97/21431 and WO 96/18402, the entire contents of which are incorporated herein by this reference. Other examples of complexes which may act as inhibitors are as follows:

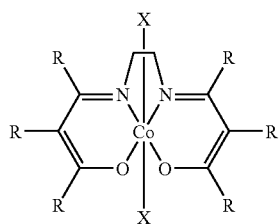

I

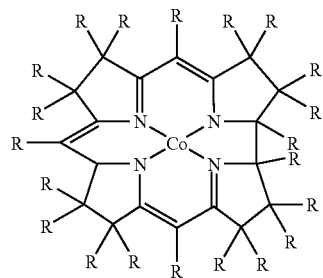

II

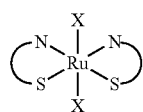

III

In formulae I, II and III, the X and R groups may be any suitable leaving or targeting groups. For example, X and R may be the same or different, and include, without being limited to, the group consisting of: ammine; amine; peptide; halogen (chloride, fluoride or iodide); nucleobase; imidazole; H$_2$O; hydrogen; saturated or unsaturated alkyl, alcohol, or carboxylate of 1 to 10 carbon atoms; aromatic; or heterocyle of up to four rings.

Other preferred compounds include cobalt(I1) phthalocyanine β-form; (S,S)-(+)-N—N'-bis(3,5-di-tert-butylsalicylidene)-1-2-cyclohexane diamino manganese (III) chloride; iron(II) phthalocyanine bis(pyridine) complex; iron(III) phthalocyanine chloride; manganese(II) phthalocyanine; 5,10,15,20-tetraphenyl-21H, 23H-porphine manganese (III) chloride; chloro(pyridine) bis (dimethylglyoximato) cobalt (III); N—N'-bis(salicylidene)dianilino-cobalt(II); cis-bis(2-2'-bipyridine)dichloro-ruthenium (II) hydrate; and cobalt (acacen)(NH$_3$)$_2$)Cl, in which (H$_2$acacen represents bis(acetylacetone)-ethylenediamine).

Compounds which are designed or selected according to the methods of the invention may be tested for inhibitory activity by any suitable assay procedure. Assays to determine the binding of metal complexes to Aβ may be performed by NMR or UV-Visible spectroscopy, or by ESR in the case of paramagnetic metals. Assays are available for measuring Cu/Fe reduction, hydrogen peroxide, hydroxyl radical generation, and carbonyl group, all of which assess the redox capacity of Aβ in the presence of Cu and Fe. Ex vivo assays using post mortem brain tissue may also be performed. These include measuring the amount of Aβ which is solubilised and extracted in the presence of the compound, and determining the quantity of peroxide formed in post mortem brain tissue, as compared with control tissue which is solubilised and extracted in the absence of the compound. Suitable methods are described for example in PCT/US99/05291 (W099/45907).

The invention will now be described in detail by way of reference only to the following non-limiting examples and to the drawings.

Materials and Methods

NMR Spectroscopy

Samples of Aβ1-40 and Aβ1-28 in aqueous solution were prepared by dissolving 0.5 mgs and 1.0 mgs respectively in 0.55 ml of 10% $^2$H20/90% H$_2$0, 100 mM KCl and 50 mM phosphate buffer. pH values were measured at room temperature, and were not corrected for isotope or solvent effects. The 1H chemical shifts were referenced to 2,2-dimethyl-2-silapentane-5-sulphonate at 0 ppm, via the chemical shift of the H$_2$0 resonance (Wishart et al., 1995a) or an impurity at 0.15 ppm.

Spectra were recorded on a Bruker DRX-600 spectrometer. All spectra in aqueous solution were recorded at 271 K and pH 6.8, with probe temperatures calibrated according to the method of van Geet (1970). All 2D spectra were recorded in phase-sensitive mode using time-proportional phase incrementation (Marion & Wuthrich, 1983). Water suppression was achieved using pulsed field gradients with the WATERGATE scheme and a 3-9-19 selective pulse (Sklenar et al., 1993).

2D homonuclear NOESY spectra (Anil-Kumar et al., 1980; Macura et al., 1981) were recorded with mixing times of 50 and 250 ms. TOCSY spectra (Braunschweiler & Ernst, 1983) were recorded using the DIPSI-2 spin-lock sequence (Rucker & Shaka, 1989) with spin-lock times of 70-80 ms. DQF-COSY (Rance et al., 1983) spectra were also recorded. Typically, spectra were acquired with 400-600 t$_1$ increments, 32-128 scans per increment, and 4096 data points. The $^1$H sweep width was 7575.6 Hz at 600 MHz. Spectra were processed using UXNMR-941001.4 (Bruker) and analyzed using XEASY 1.3.7 (Bartels et al., 1995). Sine-squared window functions, phase shifted by 60°-90°, were applied in both dimensions prior to Fourier transformation.

The $^3J_{NHC\alpha H}$ coupling constants were measured from a DQF-COSY spectrum or by using the INFIT module of XEASY to analyze NOESY spectra.

For $^3J_{NHC\alpha H}$ coupling constants measured from a DQF-COSY the appropriate rows were extracted from the spectrum, inverse Fourier transformed, zero filled to 32 K data points, and multiplied by a Gaussian window function prior to Fourier transformation. The dispersive peak shapes were simulated to take account of the effect of broad linewidths on small coupling constants, using an in-house program, COUPLING.

Metal Binding Studies

Metal binding studies were performed by titrating concentrated metal solutions (30 mM $CuCl_2$, $ZnCl_2$ in water) into the peptide solutions described above. The displacement of bound $Cu^{2+}$ from Aβ1-28 by the Co(III) Schiff-base was performed by adding two equivalents of $Cu^{2+}$ to Aβ1-28, followed by one equivalent of Co(III) Schiff-base.

Brain Tissue Assays

Tissue Selection

Post-mortem tissues, stored at −80° C., were obtained from the NH&MRC-supported Brain Bank at the University of Melbourne, together with accompanying histopathological and clinical data. AD was assessed according to CERAD criteria (Mirra et al, 1991). In order to examine the chemical architecture of the Aβ deposition observed in non-AD aged brain, Aβ immunohistochemistry was used to select age-matched control (AC) cases which did not fulfil the CERAD criteria, and in which amyloid deposition, if present, was detectable only in the form of diffuse plaques, but not neuritic plaques.

Preparation of Compounds

Compounds were dissolved in DMSO and diluted in a PBS mixture. Insoluble material was removed.

Sample Preparation:

The cortical meninges were removed and gray matter (0.5 g) was homogenised using a DIAX 900 homogeniser (Heidolph & Co, Kelheim, Germany) for 3×30 s periods at full speed, with a 30 s rest between strokes, in 3 ml of ice-cold phosphate-buffered saline (PBS), pH 7.4, containing a mixture of protease inhibitors (BioRad, Hercules, Calif.), but without ethylene diamine tetraacetic acid (EDTA), or in the presence of test compounds or metal ions prepared in PBS. The homogenate samples were incubated for 24 h at room temperature. To obtain the PBS-extractable fraction, the homogenate was centrifuged at 100,000×g for 30 min, the supernatant removed, and divided into 1 ml aliquots. Protein in a 1 ml supernatant sample was precipitated using 1:5 ice-cold 10% trichloracetic acid (TCA), and pelleted by centrifugation at 10,000×g for 20 mins. The pellet was prepared for PAGE by boiling for 10 min in Tris-tricine SDS-sample buffer containing 8% SDS, 10% mercaptoethanol and 8M urea. Total Aβ in the cortical samples was obtained by homogenizing in 1 ml PBS and boiling in sample buffer as described above.

Polyacrylamide Gel Electrophoresis (PAGE) and Western Blotting

Tris-tricine PAGE was performed by loading samples on to 10-20% gradient gels (Novex, San Diego, Calif.), followed by transfer on to 0.2 mm nitrocellulose membrane (BioRad, Hercules, Calif.). The Aβ was detected using the following monoclonal antibodies: W02, which detects Aβ40 and Aβ42 at an epitope between residues 5 and 8; G210, which is specific for Aβ species which terminate at carboxyl residue 40; or G211, which is specific for Aβ species which terminate at carboxyl residue 42 (Ida et al, 1996), in conjunction with horseradish peroxidase(HRP)-conjugated rabbit anti-mouse IgG (Dako, Denmark), and visualised using chemiluminescence (ECL, Amersham Life Science, UK). Each gel included two or more lanes containing known quantities of synthetic Aβ (Keck Laboratory, Yale University New Haven, Conn.) as reference standards. Blot films were scanned using a Relisys scanner with transparency adapter (Tech Information Systems, Taiwan) and densitometry performed using Image 1.6 software (NIH, Bethesda, Mass.). All samples were analysed at least twice, and gel loadings and dilutions adjusted to fit within the quantifiable region of the standard curve.

The efficiency of the TCA precipitation procedure was validated by testing samples of whole human serum diluted 1:10 to which had been added 2 mg of synthetic Aβ 1-40 or Aβ 1-42. Aβ recovery was assessed by extracting the precipitate into SDS sample buffer and performing Western blot analysis, using synthetic Aβ standards as described above. Protein in the TCA pellet was estimated by resuspending the pellet in water and assaying the protein recovery using a BCA assay (Pierce, Rockford, Ill.). This indicated that the efficiency of protein and Aβ precipitation was approximately 90%. The efficiency of the 8M urea solubilization was found to be equivalent to that of formic acid in a parallel, blinded assay conducted independently. All chemicals were obtained from Sigma (St. Louis, Mo.) unless otherwise indicated.

Example 1

Characterisation of Aβ Peptides in Aqueous Solution

In aqueous solution there is little chemical shift difference between the amide and $C^\alpha H$ protons of Aβ1-28 compared with Aβ1-40, suggesting that both peptides are in a similar conformation. Comparisons of A1-28 and Aβ1-40 chemical shifts with random coil chemical shifts and the lack of NOE connectivities in the NOESY spectra indicate that both peptides are mostly in conformational exchange. However, there are some medium range NOE connectivities (1</ii-j/<5) observed in the region of residues 16-21 of the peptide (KLVFFA) (SEQ ID NO: 1), suggesting that this region of the peptide has a structured turn. This is illustrated in FIG. 1.

This region of the peptide has previously been shown to be very important in defining the aggregation properties of Aβ (Hilbich et al. 1992), with the substitution of hydrophilic residues into this region resulting in altered aggregation properties, including reduced β-sheet content. In addition, several groups have described short peptides or slight variants thereof corresponding to this region which have the ability to bind to Aβ and to inhibit the formation of amyloid fibrils (Findeis et al. 1999; Tjernberg et al. 1999). This evidence implies that this "structured" section of Aβ is important in the formation of amyloid fibrils.

Example 2

Metal Binding Studies

Figure 2:
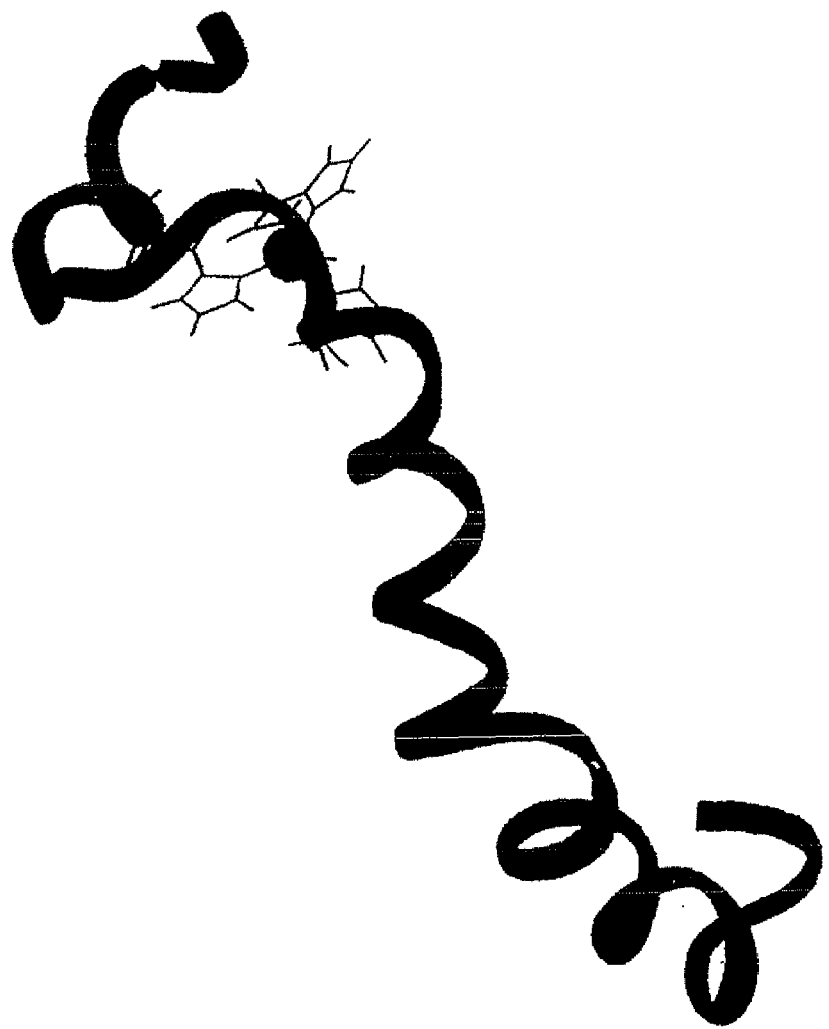
FIG. 2 shows a model of Zn bound to the three histidine residues of Aβ1-40.

To determine the metal-binding site of Aβ1-40, $Zn^{2+}$ was titrated into a solution of Aβ1-40 in SDS-micelles at pH 6.5. Peaks due to the C2H protons of the imidazole rings of His6, His13 and His14 broadened out such that they were no longer visible when a small amount of Zn solution (~25% of one mol. equivalents) was added. The addition of extra Zn (up to two mol. equivalents) did not change the spectrum, but when the pH of the solution was raised to 7.4 three broad overlapping peaks due to the C2H protons of the imidazole rings of His6, His13 and His14 became visible. These peaks did not sharpen significantly even upon the addition of a large excess of Zn (>150 mol. equivalents). There appear to be no significant difference in the rest of the spectrum between the Zn-bound and free forms of Aβ1-40, suggesting that there are no significant conformational changes upon metal binding. These results indicate that all three histidine residues of Aβ1-40 are involved in Zn binding. FIG. 2 shows a model of Zn bound to the three histidine residues of Aβ1-40.

Figure 3:
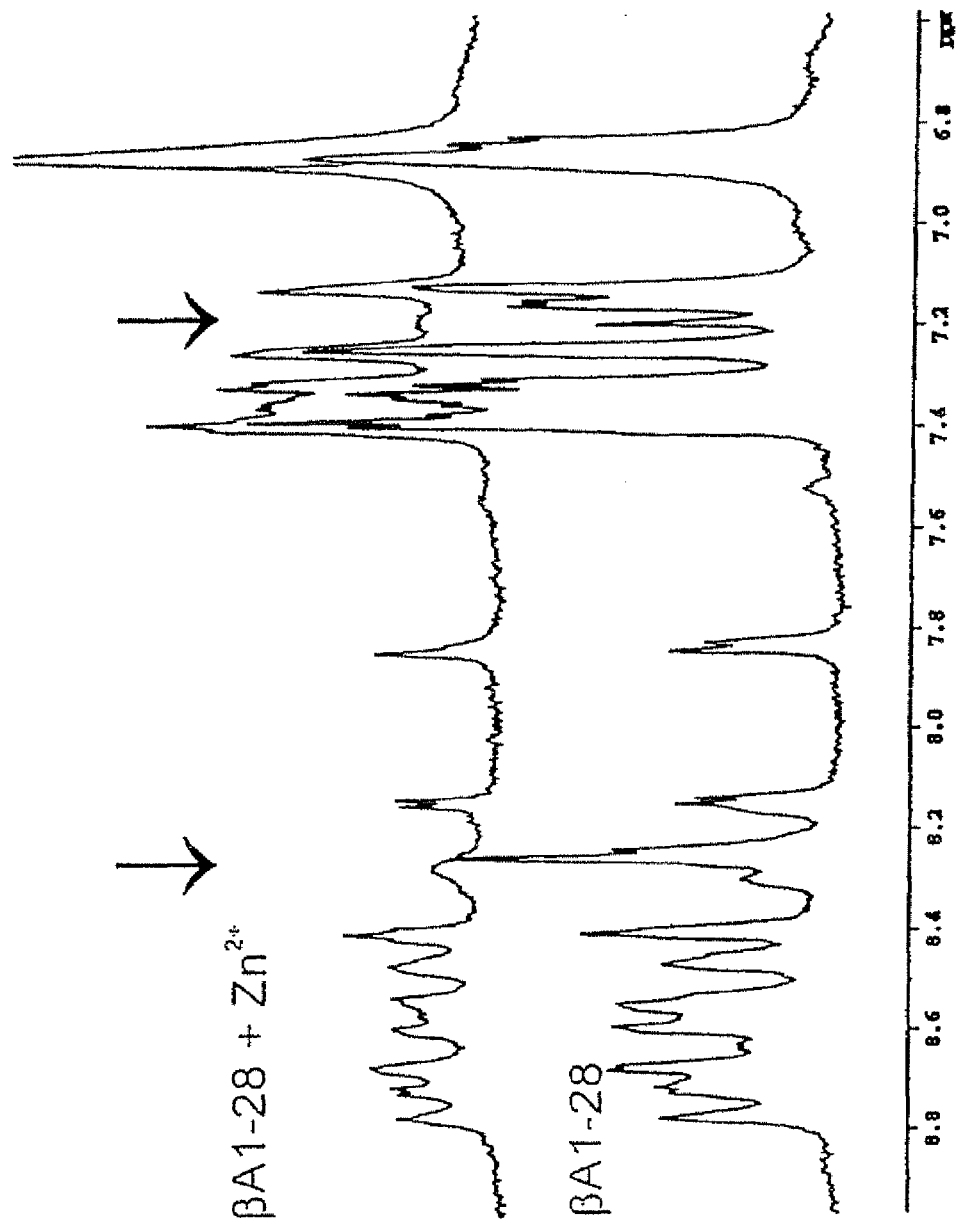
FIG. 3 is a NMR spectrum showing the effect of $Zn^{2+}$ binding to Aβ1-28.
Figure 4:
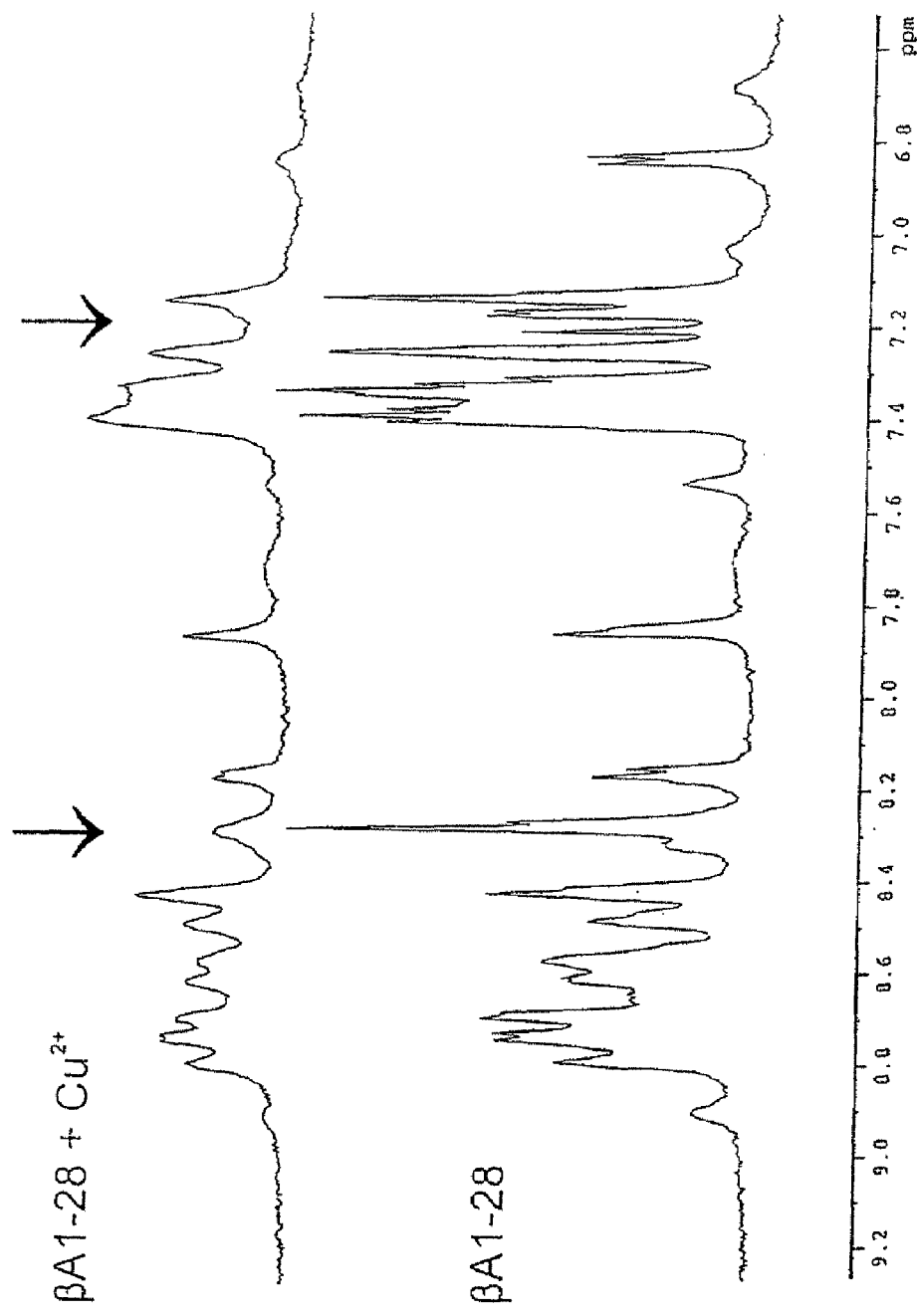
FIG. 4 is a NMR spectrum showing the effect of $Cu^{2+}$ binding to Aβ1-28.

To determine the metal-binding site of Aβ1-40 and Aβ1-28 in aqueous solution, $Zn^{2+}$ and $Cu^{2+}$ were titrated into solutions of Aβ1-40 and Aβ1-28 at pH 6.9. All reactions were accompanied by significant precipitation. The NMR spectrum of the peptide-metal complex which remained in solution showed that peaks due to the C2H and C4H protons of His6, His13 and His14 broadened out such that they were no longer visible, indicating that these residues were involved in metal binding. This is illustrated in FIGS. 3 and 4. The addition of more metal ion resulted in more precipitation, so that saturated binding was not possible.

Figure 5:
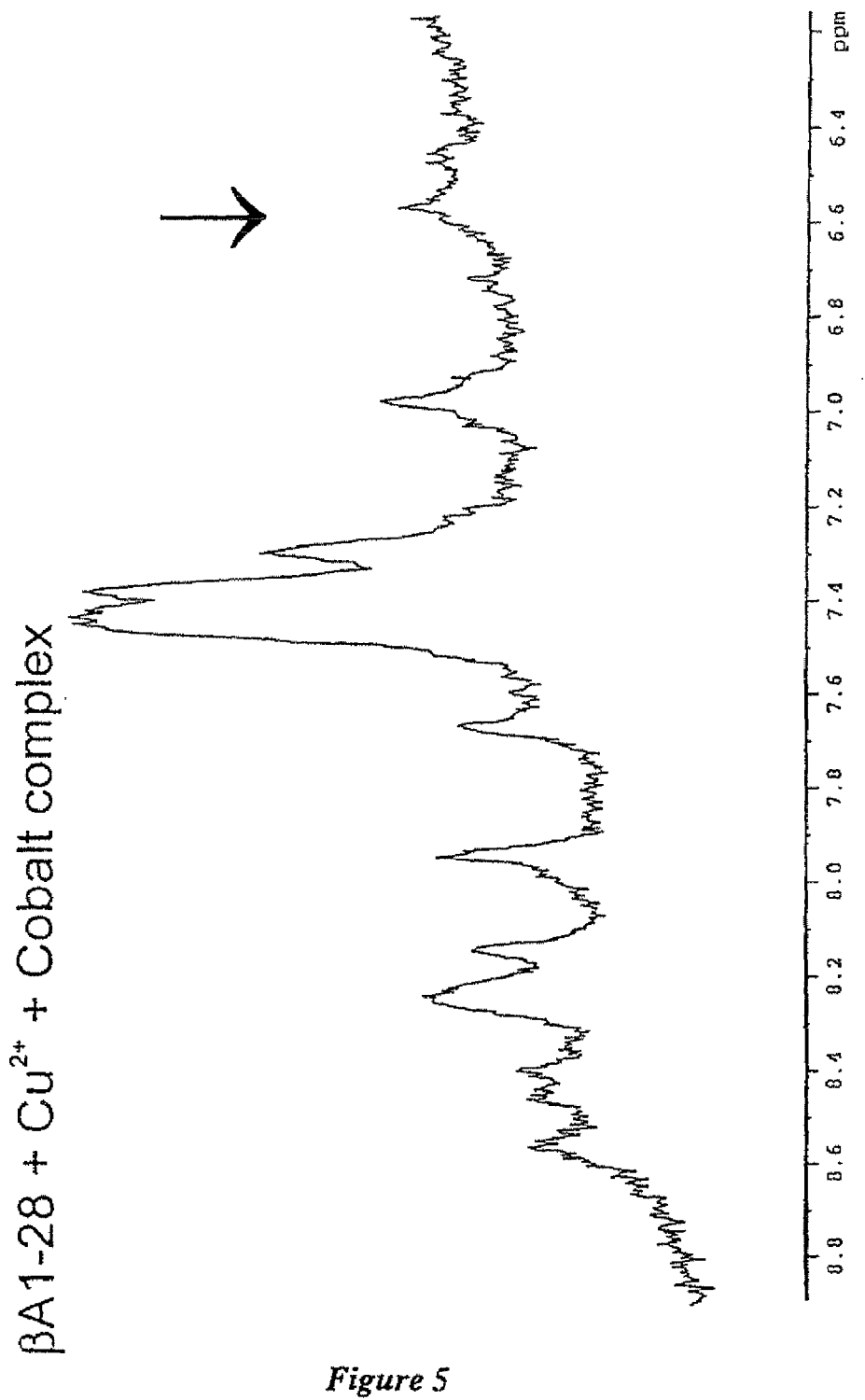
FIG. 5 is a NMR spectrum showing the effect of addition of $Cu^{2+}$ and cobalt complex to Aβ1-28.
Figure 6:
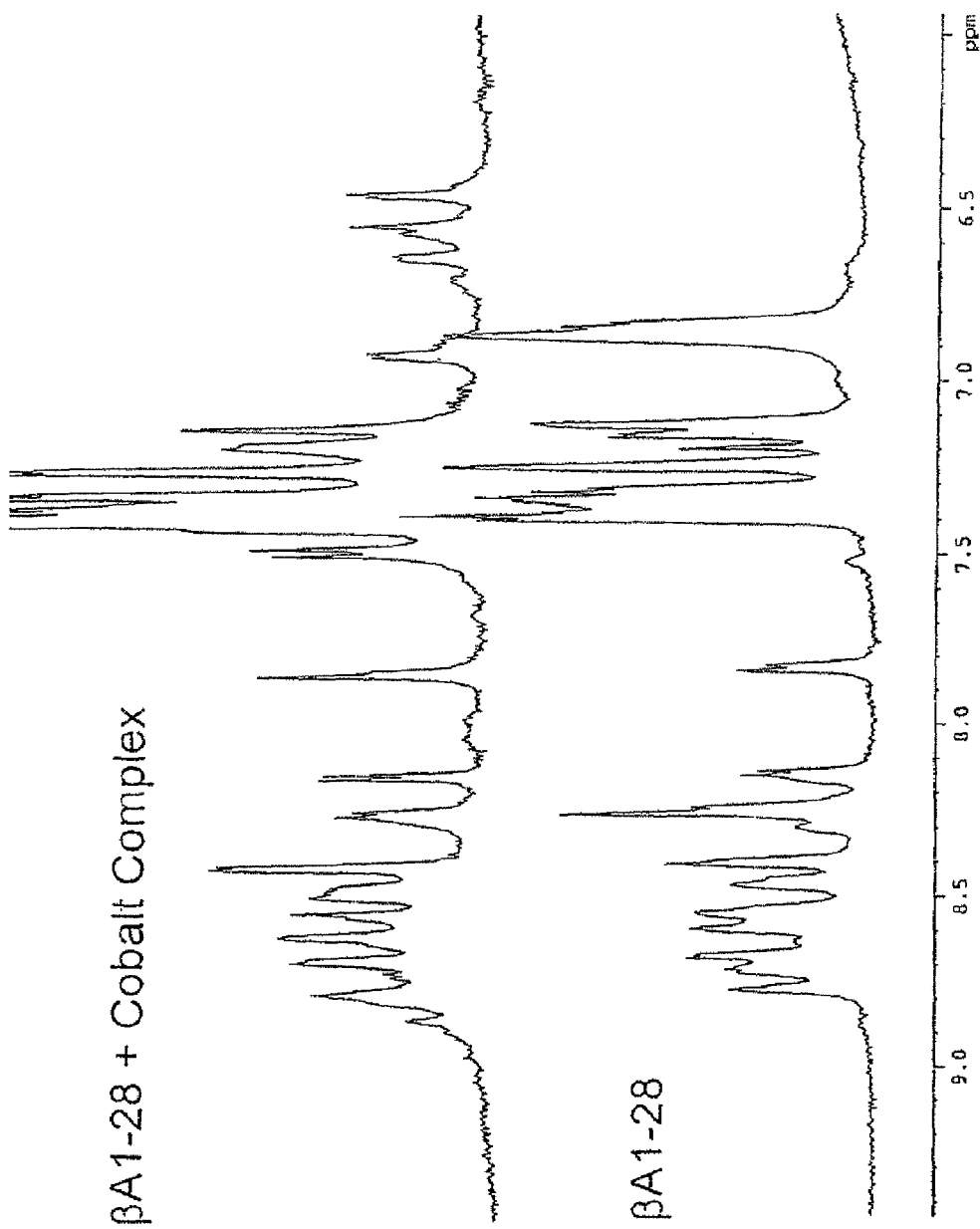
FIG. 6 is a NMR spectrum showing the binding of the cobalt complex to Aβ1-28.

When the Co(III) Schiff-base complex was added to a solution containing $Cu^{2+}$-bound Aβ1-28, a broad peak appeared in the 1H spectrum at 6.55 ppm, as shown in FIG. 5. The chemical shift of this peak is consistent with the chemical shift of a C4H proton of a histidine imidazole bound to a Co(III) Schiff-base complex, as shown in FIG. 6. This indicates that the Co(III) Schiff-base complex can compete with $Cu^{2+}$ for the histidine residues of Aβ.

Example 3

Brain Tissue Assays

Brain tissue assays were conducted in order to test the ability of the following compounds to reduce β-amyloid peptide aggregation:

| | |
|---|---|
| KJB001 | Co(II) phthalocyanine β-form |
| KJB002 | (S,S)-(+)-N-N'-bis(3,5-di-tert-butylsalicylidene)-1-2-cyclohexane diamino manganese(III) chloride |
| KJB003 | Haemin |
| KJB004 | Iron(II) phthalocyanine bis(pyridine) complex |
| KJB005 | Iron(III) phthalocyanine chloride |
| KJB006 | Manganese(II) phthalocyanine |
| KJB007 | 5,10,15,20-tetraphenyl-21H,23H-porphine manganese(III) chloride |
| KJB008 | Chloro(pyridine) bis(dimethylglyoximato)cobalt (II) |
| KJB009 | N-N'-bis(salicylidene)dianilino-cobalt(II) |
| KJB010 | cis-bis(2-2'-bipyridine)dichloro-ruthenium(II) hydrate. |
| BRI6805 | [Co(acacen)(NH3)2]Cl (H2acacen represents bis(acetylacetone)ethylenediamine) |

Table 1 shows the approximate concentration of each compound used in the extraction.

TABLE 1

| Compound | Concentration (μmol/liter) |
|---|---|
| KJB001 | 0.0105 |
| KJB002 | 4.41 |
| KJB003 | 60.87 |
| KJB004 | 3.816 |
| KJB005 | 3.08 |
| KJB006 | 111.5 |
| KJB007 | 0.64 |
| KJB008 | 1289.9 |

TABLE 1-continued

| Compound | Concentration (μmol/liter) |
|---|---|
| KJB010 | 300.9 |
| BRI6805 | 1199.9 |
| bathocuproine | 2000 |

Figure 7:
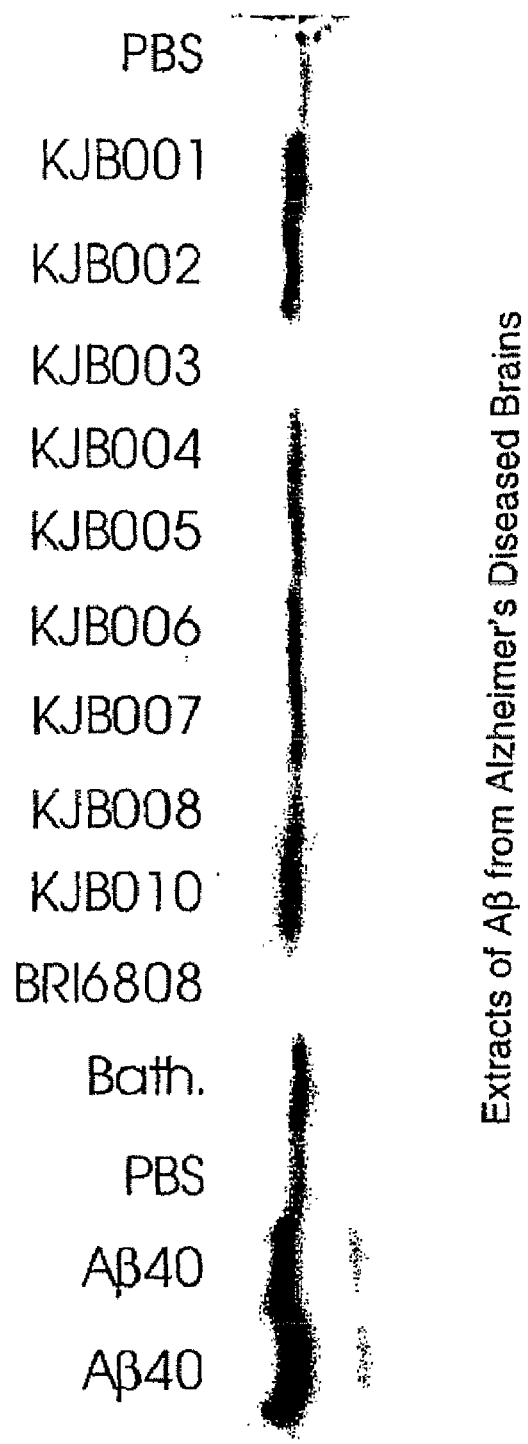
FIG. 7 is a Western blot showing results of brain tissue assays testing the ability of a range of metal compounds to solublilize Aβ deposits.

The results presented in FIG. 7 clearly demonstrate that some of the metal complexes have the ability to solubilise Aβ deposited in the brains of Alzheimer's disease patients. In particular, compound KJB001 showed particularly strong solubilising activity, and compounds KJB002, KJB005, KJB006, KJB007 and KJB010 also showed good activity.

Example 4

Compounds Designed to Bind One or More of the Three Histidine Residues in Aβ

BRI7080, BRI7103 and BRI7104 are metal complexes of aza-macrocycles of the following structures.

a) BRI7080

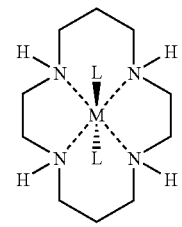

BRI7080: M = $Ni^{2+}$ L = $H_2O$ $Ni(NO_3)_2 \cdot 6H_2O$ (1.67 g, 5.75 mmol) was added in portions to a solution of 1,4,8,11-tetraazacyclotetradecane (1.0 g, 5.00 mmol) in ethanol (50 ml) at 50° C. The mixture was heated at 50° C. for 2 h during which time the green coloured nickel salt dissolved to give a red solution. Upon cooling of the crude reaction mixture to room temperature, a purple solid had precipitated which was collected by filtration and washed with several portions of 2-propanol. The product thus obtained was dried overnight in a vacuum oven. Spectral and analytical data acquired for this compound were in agreement with literature data.

(b) BRI7103

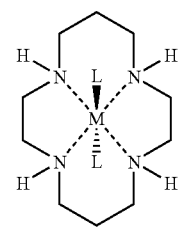

BRI7103: M = $Mn^{3+}$ L = Cl

BRI7103 was prepared following the method of P-K. Chan and C-K. Poon, *J. C. S. Dalton Trans.*, 1976, 858-862.

(c) BRI7104

This compound has similar structures to BRI7080 and BRI7103, but in this case M=Co³⁺ and L=Cl.

BRI7104 was prepared following the method of P-K. Chan and C-K. Poon, *J. C. S. Dalton Trans.*, 1976, 858-862.

Example 5

Histidine Binding Compounds Conjugated with an Aβ-Directing Group

For the second class of molecules we chose derivatives of the pentapeptide leucine-valine-phenylalanine-phenylalanine-alanine (LVFFA) (SEQ ID NO: 2), designated herein as BRI7082 and BRI7077, to direct histidine binding compounds to Aβ.

BRI7106 is an example of a nicotine derivative conjugated to an Aβ-directing group. In this example the histidine-binding group is a small organic molecule rather than a metal complex, in contrast to most of the compounds described above. BRI7158 and BRI7159 are examples of metal complexes conjugated to an Aβ-directing group.

(a) BRI7082

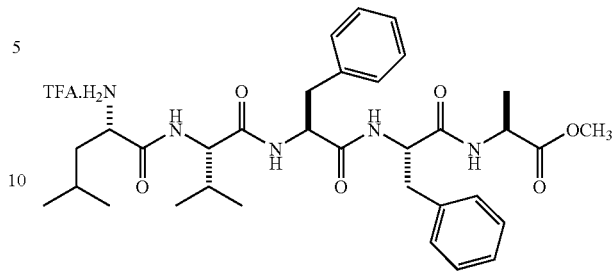

BRI7082

BRI7082 was prepared via standard HBTU-mediated peptide coupling methodology; see M. Bodanszky and A. Bodanszky, *"The Practice of Peptide Synthesis"*, 2$^{nd}$ Edition, Springer-Verlag, 1994.

Mass Spectrum (APCI) m/z 610 [(MH—C$_2$HO$_2$F$_3$)$^+$, 100%].

(b) BRI7106

This compound was synthesised according to Reaction Scheme 1:

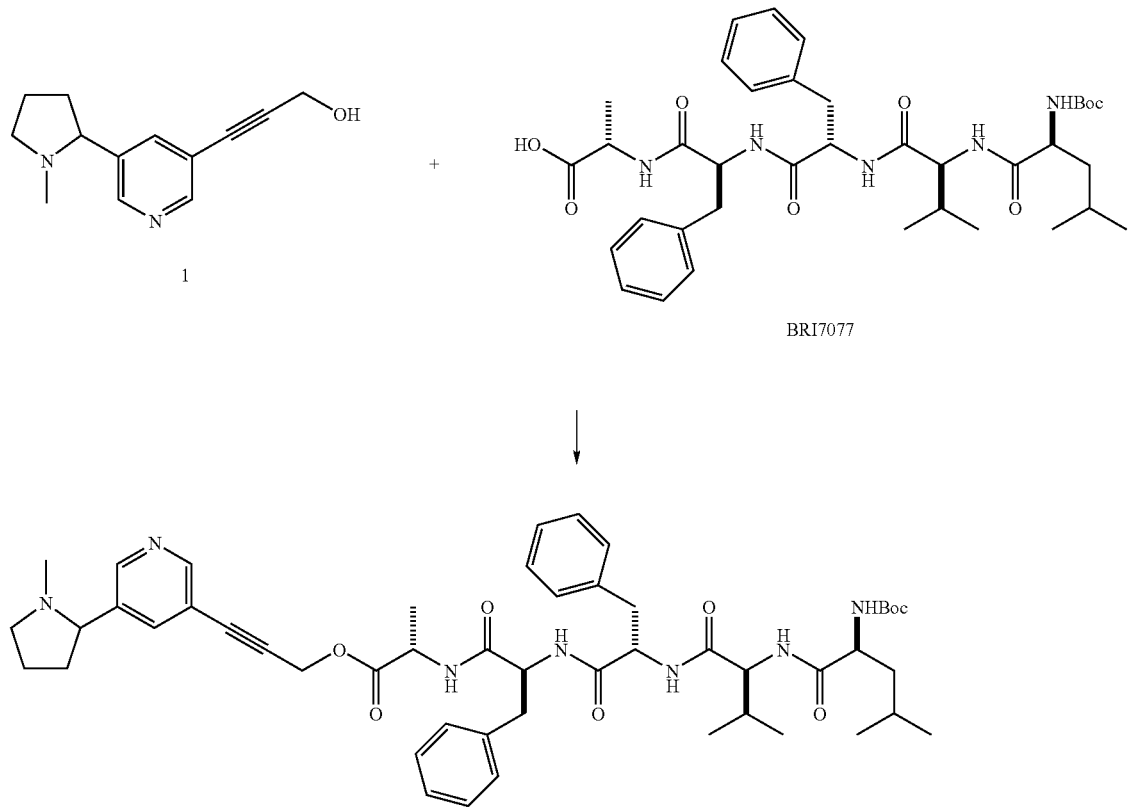

Compound 1 was prepared following the methods of P. Jacob III, *J. Org. Chem.*, 1982, 47, 4165-4167 and N. D. P. Cosford et al., *J. Org. Chem.*, 1998, 63, 1109-1118. Mass Spectrum (APCI) m/z 217 [(M+H)$^+$, 100%].

BRI7077 was prepared via standard HBTU-mediated peptide coupling methodology; see M. Bodanszky and A. Bodanszky, "*The Practice of Peptide Synthesis*", 2$^{nd}$ Edition, Springer-Verlag, 1994.

Mass Spectrum (APCI) m/z 696 [(M+H)$^+$, 20%], 694 [(M−H), 95%].

BRI7106 was prepared via standard DCC-mediated esterification methodology; see M. Bodanszky and A. Bodanszky, "*The Practice of Peptide Synthesis*", 2$^{nd}$ Edition, Springer-Verlag, 1994.

Mass Spectrum (APCI) m/z 894 [(M+H)$^+$, 10%], 892 [(M−H), 25%].

(c) Synthesis of BRI7158

This compound was synthesised according to Reaction Scheme 2:

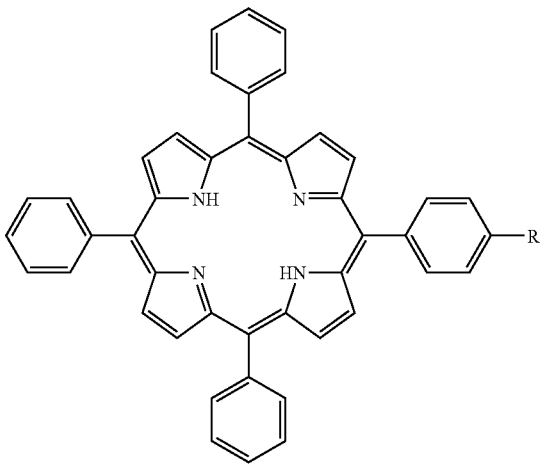

2a: R = CO$_2$H

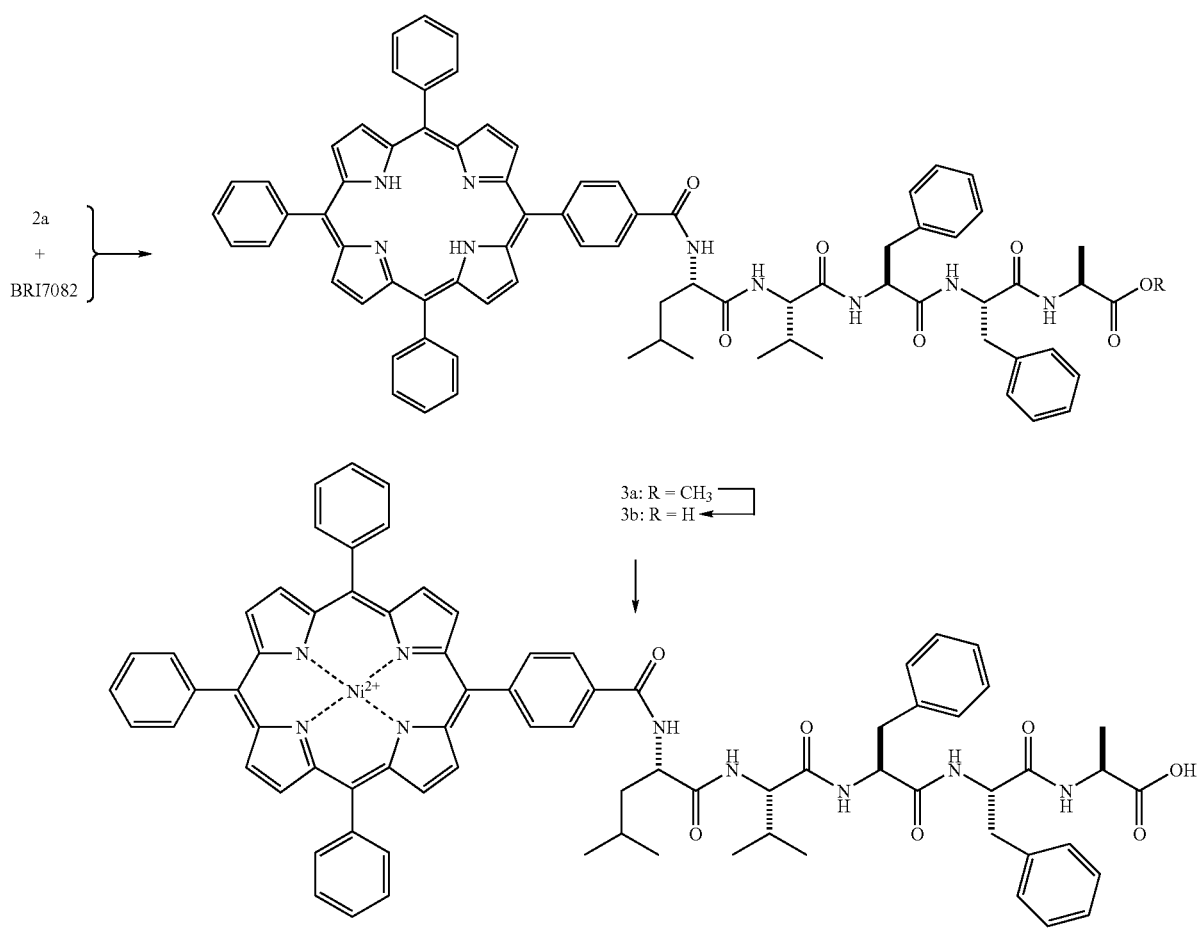

Porphyrin 2a was prepared following the methods of K. Nakanishi et al., *Heterocycles*, 1996, 42, 723-736 and D. A. James et al., *Bioorg. Med. Chem. Lett.*, 1999, 9, 2379-2384.

N-Diisopropylethylamine (0.10 ml, 0.57 mmol) was added to a magnetically stirred mixture of porphyrin 2a (118 mg, 0.18, mmol), HBTU (68 mg, 0.18 mmol), and BRI7082 (130 mg, 0.18 mmol) in dry DMF (4 ml) under an atmosphere of nitrogen. Stirring was continued at room temperature for 16 h, after which time, the crude reaction mixture was partitioned between ethyl acetate and brine. The separated organic layer was successively washed with 10% aqueous citric acid solution, saturated aqueous NaHCO$_3$ solution and brine before being dried (MgSO$_4$), filtered and concentrated under reduced pressure to afford compound 3a as a deep purple, crystalline solid.

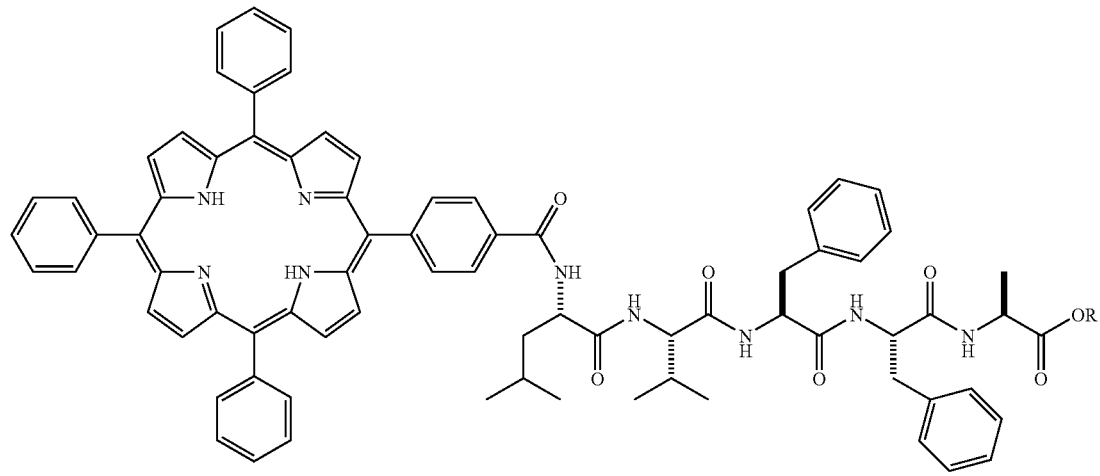

3a: R = CH$_3$

Mass Spectrum (APCI) m/z 1250 [(M+H)$^+$, 45%].

A solution of compound 3a (23.3 mg, 0.019 mmol, THF (0.5 ml), methanol (50 drops) and 2M aqueous NaOH solution (0.1 ml) was stirred at room temperature for 18 h. The crude reaction mixture was partitioned between ethyl acetate and water and the phases separated. The aqueous layer was acidified to pH 4 upon the addition of 10% aqueous citric acid solution and then extracted three times with ethyl acetate. The combined organic layers were dried (MgSO$_4$), filtered and concentrated under reduced pressure to afford compound 3b as a purple solid.

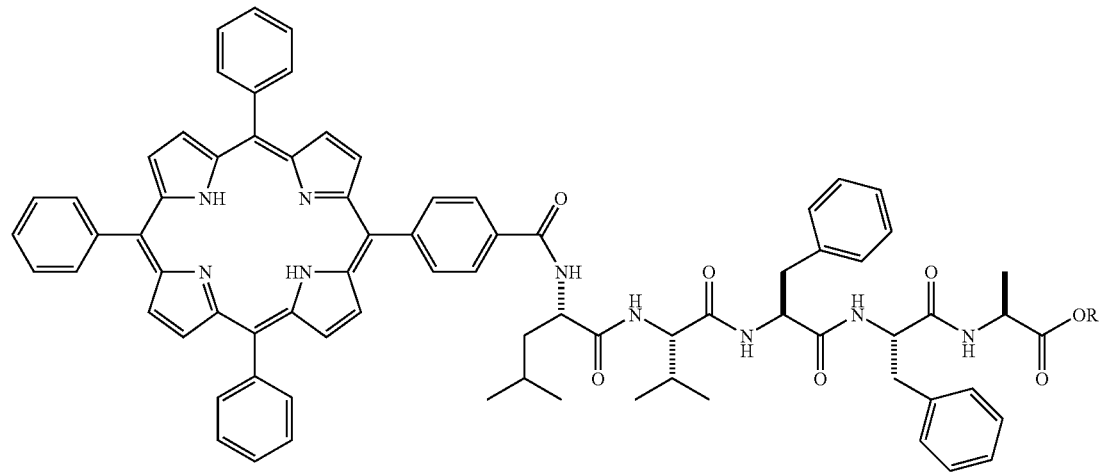

3b: R = H

Mass Spectrum (APCI) m/z 1236 [(M+H)$^+$, 30%].

A magnetically stirred mixture of compound 3b (17 mg, 0.014 mmol), Ni(OAc)$_2$.4H$_2$O (34.2 mg, 0.14 mmol), glacial acetic acid (0.73 ml) and dichloromethane (1.45 ml) was heated at reflux under an atmosphere of nitrogen for 18 h. The now crimson red reaction mixture was cooled to room temperature and partitioned between ethyl acetate and 10% aqueous NaHCO$_3$ solution. The separated aqueous phase was extracted three times with ethyl acetate before being dried (Na$_2$SO$_4$), filtered and concentrated under reduced pressure to give a red solid. Subjection of this material to flash chromatography (silica, 10% methanol/dichloromethane elution) afforded, after concentration of the appropriate fractions (R$_f$ 0.30), BRI7158 as a red, crystalline solid.

Mass Spectrum (ES) m/z 1291 [(M−H), <10%].

(d) Synthesis of BRI7105 and BRI7159

These compounds were synthesised according to Reaction Scheme 3:

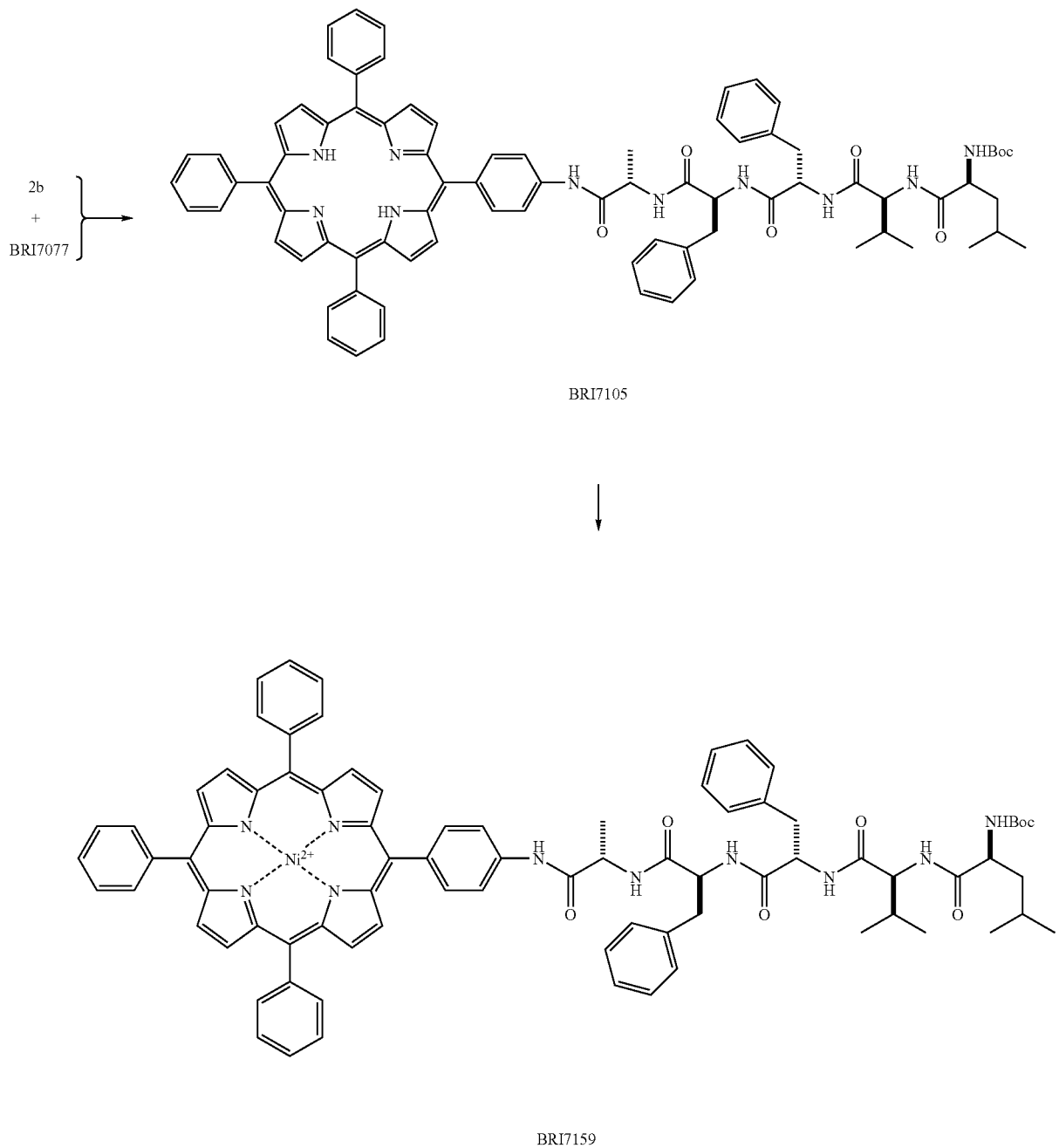

Porphyrin 2b was prepared following the method of W. J. Kruper, Jr. et al., *J. Org. Chem.*, 1989, 54, 2753-2756.

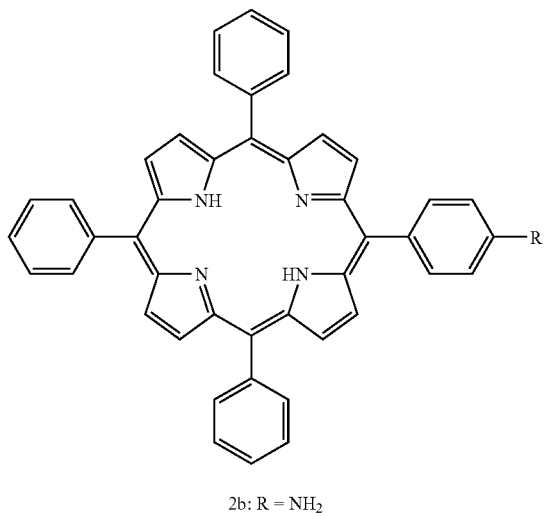

2b: R = NH$_2$

N,N-Diisopropylethylamine (0.21 ml, 1.18 mmol) was added at room temperature to a magnetically stirred mixture of porphyrin 2b (151 mg, 0.24 mmol), HBTU (216 mg, 0.58 mmol), and BRI7077 (200 mg, 0.29 mmol) in dry DMF (2 ml) under an atmosphere of nitrogen. Stirring was continued at 40° C. for 40 h, after which time the crude reaction mixture was partitioned between ethyl acetate and brine. The separated organic layer was successively washed with 10% aqueous citric acid solution, 5% aqueous NaHCO$_3$ solution and brine before being dried (MgSO$_4$), filtered and concentrated under reduced pressure to afford a deep purple glass. Subjection of this material to flash chromatography (silica, 1% to 5% methanol/dichloromethane elution) gave, after concentration of the relevant fractions (R$_f$ 0.35), BRI7105 as a purple, crystalline solid.

Mass Spectrum (APCI) m/z 1307 [(M+H)$^+$, <5%].

A magnetically stirred mixture of BRI7105 (47 mg, 0.04 mmol), Ni(OAc)$_2$.4H$_2$O (96 mg, 0.39 mmol), glacial acetic acid (2 ml) and dichloromethane (4 ml) was heated at reflux under an atmosphere of nitrogen for 18 h. The now crimson red reaction mixture was cooled to room temperature and partitioned between ethyl acetate and 10% aqueous NaHCO$_3$ solution. The separated aqueous phase was extracted three times with ethyl acetate before being dried (Na$_2$SO$_4$), filtered and concentrated under reduced pressure to give a red solid. Subjection of this material to flash chromatography (silica, 10% methanol/dichloromethane elution) afforded, after concentration of the appropriate fractions (R$_f$ 0.30), BRI7159 as a red, crystalline solid.

Mass Spectrum (APCI) m/z 1385 [(M+Na)$^+$, <5%].

(e) Synthesis of BRI7160 and BRI7161

The compounds were prepared according to Reaction Scheme 4:

Scheme 4

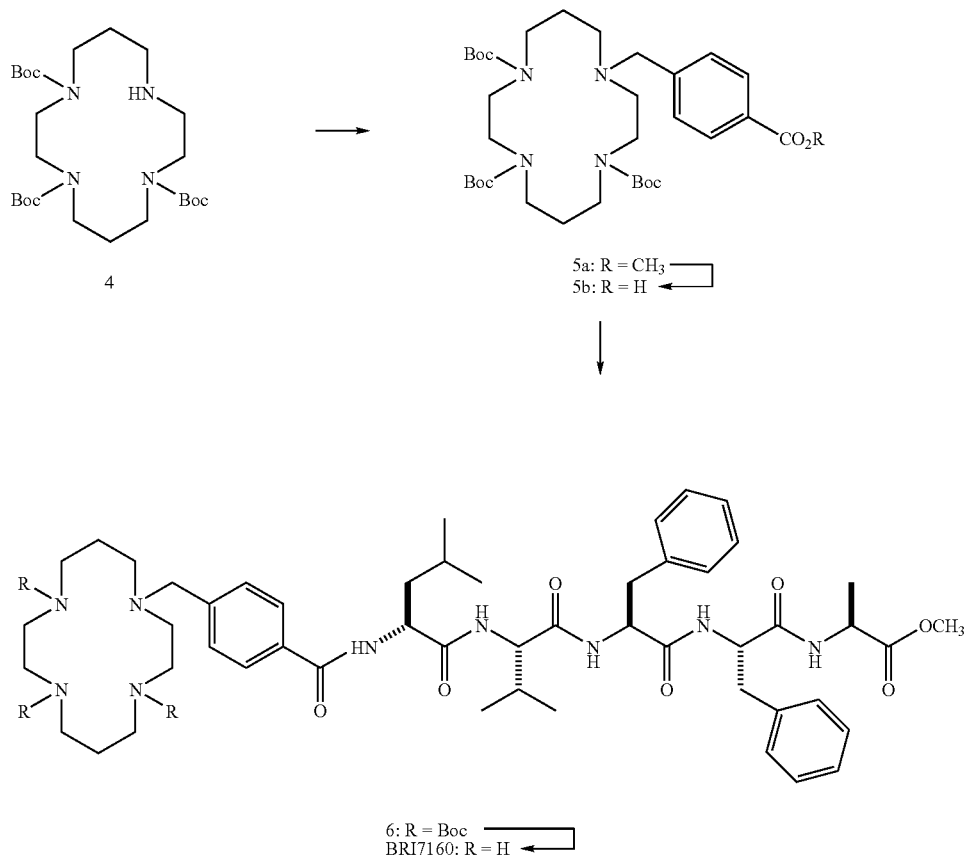

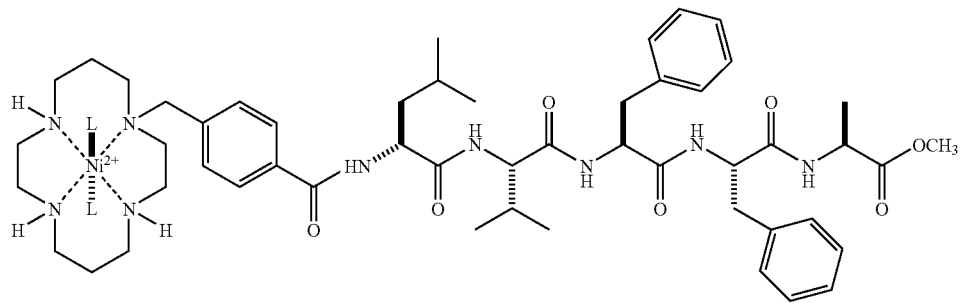

BRI7161 L = H₂O

Compound 4 was prepared following the method of R. Guilard et al., *Bull. Soc. Chim. Fr.*, 1996, 133, 65-73.

A magnetically stirred suspension of compound 4 (430 mg, 0.86 mmol), (4-bromomethyl) methyl benzoate (217 mg, 0.95 mmol), KHCO₃ (172 mg) and K₂CO₃ (174 mg) in dry acetonitrile (17 ml) was heated at reflux for 18 h under an atmosphere of nitrogen. The reaction mixture was cooled to room temperature then concentrated under reduced pressure to yield a straw coloured oil which was purified by flash chromatography (silica, 5% methanol/dichloromethane elution). Concentration of the appropriate fractions (RF 0.38) afforded adduct 5a as a clear, colourless oil. Mass Spectrum (APCI) m/z 649 [(M+H)⁺, 100%].

A mixture of compound 5a (120 mg, 0.19 mmol), 1M aqueous LiOH (5 ml) and THF (5 ml) was magnetically stirred at room temperature for 16 h. The crude reaction mixture was partitioned between ether and water and the separated aqueous layer was cooled to 0° C. prior to acidification to pH 4 with 10% aqueous citric acid solution. Extraction of the aqueous layer with ethyl acetate, followed by drying of the organic fraction with MgSO₄ afforded, after concentration under reduced pressure, compound 5b as a viscous, colourless oil.

Mass Spectrum (APCI) m/z 633 [(M−H), 100%].

N,N-Diisopropylethylamine (0.17 ml, 0.98 mmol) was added to a magnetically stirred mixture of compound 5b (167 mg, 0.26 mmol), HBTU (132 mg, 0.35 mmol), and BRI7082 (209 mg, 0.29 mmol) in dry DMF (2 ml) under an atmosphere of nitrogen. Stirring was continued at room temperature for 16 h, after which time, the crude reaction mixture was partitioned between ethyl acetate and brine. The separated organic layer was successively washed with 10% aqueous citric acid solution, saturated aqueous NaHCO₃ solution and brine before being dried (MgSO₄), filtered and concentrated under reduced pressure to afford compound 6 as a viscous oil.

Mass Spectrum (APCI) m/z 1226 [(M+H)⁺, 65%].

A solution of compound 6 (258 mg, 0.21 mmol) in dichloromethane (4 ml) was treated with trifluoroacetic acid (0.1 ml) under an atmosphere of nitrogen and stirring was continued at room temperature for 20 h. The crude reaction mixture was concentrated under reduced pressure to afford a light tan oil which was purified by flash chromatography (silica, 6% methanol/dichloromethane elution). Concentration of the relevant fractions ($R_f$ 0.30) afforded BRI7160 as a pale yellow foam.

Mass Spectrum (APCI) m/z 633 [(M−H), 100%].

A solution of BRI7160 (41 mg, 0.044 mmol) and Ni(OAc)₂.4H₂O (103 mg, 0.41 mmol) in dry methanol (2 ml) was heated at reflux for 19 h under an atmosphere of nitrogen. The cooled reaction mixture was concentrated under reduced pressure to afford a solid residue. This material was treated with chloroform (4 ml) and the resulting suspension was filtered. Concentration of the filtrate afforded BRI7161 as a foam-like residue.

Mass Spectrum (APCI) m/z 1020 [(M+H)⁺, 30%].

Example 5

Testing of Compound KJB030 for Ability to Inhibit Amyloid β-Peptide Neurotoxicity In Vitro Compound KJB030 was dissolved in chelex 100-treated double distilled H₂O (CH100-dH₂O) at a concentration of 200 μM. Aβ1-42 was dissolved in either 200 μm KJB030 solution or in CH100-dH₂O. Both solutions contained 200 μM Aβ1-42. The Aβ1-42 solutions were incubated at ambient temperature (~20-24° C.) for 3 days. The solutions were then brought to a physiological state by adding 10× phosphate buffered saline (PBS), pH 7.4, thus bringing samples to 1×PBS. Samples were then incubated at 37° C. for 24 hr to induce aggregation of Aβ1-42. Samples were subsequently dialysed in microdialysis cups (3500 $M_r$ cut-off) placed in 5 L PBS for 24 hr, in order to remove some of the excess KJB030 without loss of Aβ1-42.

Dialyzed samples were added to six day old cerebral cortical neuron cultures growing in Neurobasal medium with B27 supplements but without anti-oxidants (Gibco). Samples were diluted into the culture medium to a final concentration of 20 μM Aβ1-42. The concentration of the KJB030 was unknown, due to dialysis of the sample; however, the maximum concentration would be 20 μM if no dialysis had occurred. Six wells of each of the following were established: 1; Untreated control cells, 2; Aβ1-42 (20 μm), 3; KJB030 (dialysed), 4; KJB030+Aβ1-42 (20 μM, dialysed), 5; vehicle only (PBS). Cultures were treated for 5 days (37° C./5% CO₂) and culture medium was removed for analysis of cell death.

Determination of cell death was performed using the lactate dehydrogenase (LDH) assay kit (Boehringer Mannheim). This is a measure of the release of LDH, a constitutively expressed, highly abundant enzyme, from dead (lysed) cells. Culture medium was mixed with the reagents from the LDH kit as per the manufacturer's instructions and the level of LDH measured colourimetrically on a spectrophotometric 96 well plate reader at 490 nm. Using the equation supplied with the LDH assay kit, the percentage of LDH release and hence cell death compared to untreated control cultures was determined. The results are shown in Table 1.

TABLE 1

Results of LDH assay for cell death

| Treatment: | % cell death |
|---|---|
| Untreated control neurons: | 0 |
| Vehicle alone (PBS) | −1.18 ± 1.4 |
| KJB030 alone | 8.1 ± 2.2 |
| Aβ1-42 (20 μM) alone | 22 ± 3.5 |
| Aβ1-42 (20 μM) + KJB030 | 3.9 ± 2.5* |

*Significantly different from Aβ1-42 alone (p < 0.01)

Example 6

Demonstration of Reaction of Compound KJB001 with Aβ1-28

1.8 mgs of Aβ1-28 was dissolved in 5 mls DMSO was mixed with 0.33 mgs of compound KJB001 (~1 equivalent) dissolved in 0.3 mls DMSO. The mixture was allowed to stand for 24 hrs before being freeze-dried. The resulting blue powder was dissolved in 550 μl of an aqueous solution containing 100 mM NaCl, 50 mM phosphate buffer, pH 6.9. A solution of 1.8 mgs Aβ1-28 dissolved in 550 μl of the same solution was used as a control.

Figure 9:
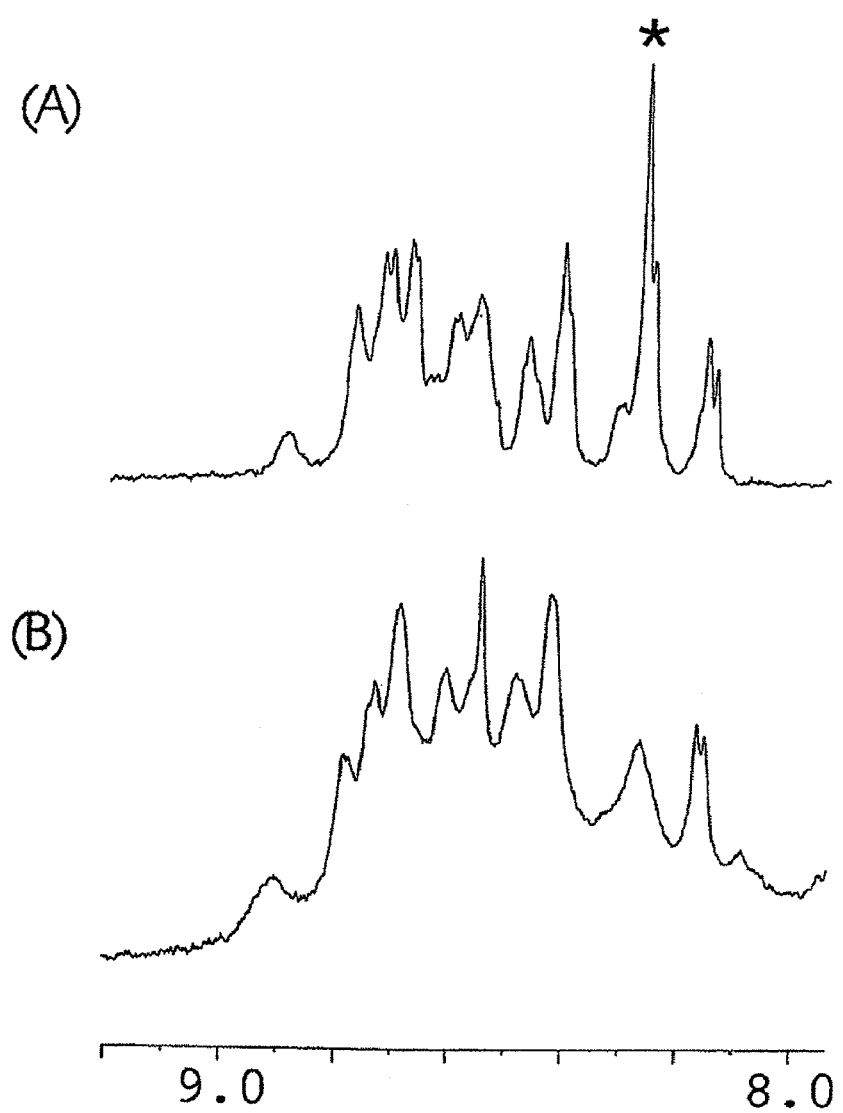
FIG. 9 shows NMR spectra demonstrating the binding of the compound KJB001 to Aβ1-28.

FIG. 9(A) shows the 600 MHz $^1$H NMR spectrum of the aqueous solution of Aβ1-28 at 271 K. The resonances due to the C2H protons of His6, 13, 14 are marked with *. FIG. 9(B) shows the $^1$H 600 MHz NMR spectrum of the solution of Aβ1-28 plus KJB001, demonstrating that the peaks due to the histidine C2H protons had shifted, thus indicating that KJB001 had reacted with these residues.

DISCUSSION

When copper and iron bind to Aβ, reactive oxygen species such as peroxide and superoxide are produced. When copper and zinc bind to Aβ, both induce aggregation, and copper binding is inhibited by zinc, suggesting that these ions bind to similar binding sites, or share a single binding site. Zinc, and presumably copper, bind to the histidine residues of Aβ. Thus a molecule which prevents the binding of zinc and copper to these histidine residues has the potential to inhibit Aβ aggregation and to prevent metal-induced neurotoxicity.

Figure 8:
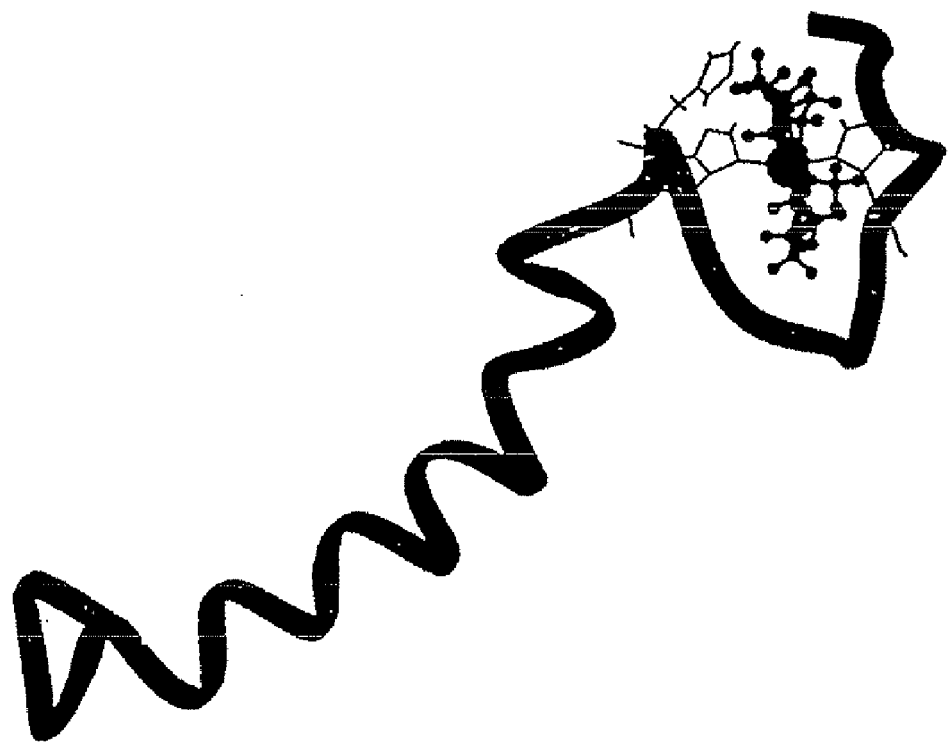
FIG. 8 shows a model of the cobalt-corrin ring complex bound to Aβ1-40.

Compounds of the kind described herein have the potential to bind to histidine residues and therefore to prevent zinc and copper binding, and so may have therapeutic value. A model of a cobalt-corrin ring complex bound to Aβ1-40 is shown in FIG. 8.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Atwood C S, Scarpa R C, Huang X, Moir R D, Multhaup G, Tanzi R E, Bush Al. 1998a.
Gain of Function of the Dutch-type mutant Ab protein: Altered copper binding and increased generation of SDS-Resistant Aβ polymers.
Abstract, 6th International Conference on Alzheimer's Disease, Amsterdam, 18-23 July.
Atwood C S, Moir R D, Huang X, Scarpa R C, Bacarra NIVE, Romano D M, lo Hartshorn M A, Tanzi R E, Bush A I. 1998b J. Biol. Chem. 273: 12817-12826.
Anil-Kumar, Ernst R R, Wilthrich K. 1980.
A two-dimensional nuclear Overhauser enhancement (2D NOE) experiment for the elucidation of complete proton-proton cross-relaxation networks in biological macromolecules. Biochem Biophys Res Commun 95: 1-6.
Bartels Q Xia T-H, Billeter M, G-intert P, Wuthrich K. 1995.
The program XEASY for computer-supported NMR spectral analysis of biological macromolecules. J. Biomol NMR 5: 1-10.
Braunschweiler L, Ernst R R. 1983.
Coherence transfer by isotropic mixing: application to proton correlation spectroscopy.
J Magn Reson 53: 521-528.
Bush A I, Huang X, Atwood C S, Cherny R A, Moir rd, Goldstein LE, O'Malley C M, Saunders A J, Multhaup G, Beyreuther K, Master C L, Tanzi R E. 1998.
Interactions with ionic zinc, copper and iron govern Aβ redox activity and accumulation in Alzheimer's disease. Abstract, 6th International Conference on Alzheimer's Disease, Amsterdam, 18-23 July.
Cherny R A, Legg J T, Beyreuther K, Tanzi R E, Master C L, Bush A I 1998.
Differential effects of chelators upon the solubilization of cerebral Aβ deposits in post-mortem Alzheimer and control brain tissue.
Abstract, 6th International Conference on Alzheimer's Disease, Amsterdam, 18-23 July.
Findeis et al. 1999.
Modified-Peptide Inhibitors of Amyloid β-Peptide Polymerisation.
Biochemistry 38: 6791-6800.
Glenner, G. G, and Wong, C W 1984.
Alzheimer's disease: initial report of the purification and characterization of a novel cerebrovascular amyloid protein, Biochem, Biophys, Res. Commun, 120: 885-890.
Hilbich, G, Kisters-Woike, B., Reed, J., Masters, C. L., and Beyreuther K. (1992)
J. Mol. Biol. 228: 460-473.
Ida, N., Hartmann, T., Pantel, J., Schroder, J., Zerfass, R., Forstl, H., Sandbrink, R., Masters, C. L. and Beyreuther, K. (1996)
J. Biol Chem 271:22908-22914.
Kang, J. Et al, 1987.
The precursor of Alzheimer's disease amyloid A4 protein resembles a cell-surface receptor.
Nature 325: 733-736.
Macura S, Huang Y, Suter D, Ernst R R. 1981.
Two-dimensional chemical exchange and cross-relaxation spectroscopy of coupled nuclear spins.
J. Magn Reson 43: 259-281.
Marion D, Wuthrich K. 1983.

Application of phase sensitive two dimensional correlated spectroscopy (COSY) for measurements of 1HAH spin-spin coupling constants in proteins.
Biochem Biophys Res Commun 113: 967-974.
Markesbery, W R 1997
Free radical Biology and Medicine, 23, 134-147.
Mirra, S. S., Heyman, A., McKeel, D., Sumi, S. M., Crain, B. j., Brownlee, L. M., Vogel, F. S., Hughes, J. P., van Belle, G. and Berg, L. (1991)
Neurology 41:479-486.
Rance M, Sorenson O W, Bodenhausen G, Wagner G, Ernst R R, Wuthrich K. 1983.
Improved spectral resolution in COSY $^1$H NMR spectra of proteins via double quantum filtering.
Biochem Biophys Res Commun 117: 479-485.
Rucker S P, Shaka Aj. 1989.
Broadband homonuclear cross-polarisation in 2D NMR using DIPSI-2.
Mol. Phys. 68: 509-517.
Tjernberg et al. 1999.
A Molecular Model of Alzheimer Amyloid β-Peptide Fibril Formation.
J. Biol. Chem. 274: 12619-12625.
Van Geet A L. (1970)
Calibration of methanol nuclear magnetic resonance thermometer a low temperature.
Anal Chem 42: 679-680.
Wishart D S, Bigam C G, Yao J, Abildgaard F, Dyson J, Oldfield E, Markley J L, Sykes B D. 1995 a.
'H, "C and "N chemical shift referencing in biomolecular 10NMR.
J. Biomol NMR 6:135-140.
Wishart D S, Sykes B D, Richards F M. 1992
The chemical shift index: a fast and simple method for the assignment of protein secondary structure through NIvM spectroscopy.
Biochemistry 31: 1647-165 1. 15
Yanker, B. A et al. 1989.
Neurotoxicity of a fragment of the amyloid precursor associated with Alzheimer's disease.
Science 245: 417-420.

The invention claimed is:

1. A method of inhibiting the binding of one or more metal ions to a β-amyloid peptide in a patient in need thereof comprising exposing the peptide in said patient to a metal complex of a 1,10-phenanthroline said metal being Mn, Co, Ni, Cu, Ru, Pd, Ag, Cd, Pt, Au, Rh or Hg, wherein the metal complex binds to at least one histidine selected from the group of His 6, His 13 and His 4 of the N-terminal loop of the β-amyloid peptide, thereby blocking the binding of $Cu^{2+}$, $Zn^{2+}$ and/or $Fe^{2+}$ ions to said at least one histidine residue.

2. The method of claim 1, wherein the metal complex has the formula

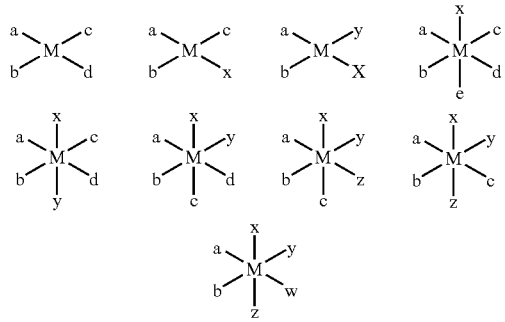

wherein a, b, d, c, and e are chelating non-leaving groups present in said 1,10-phenanthroline,
M is a metal selected from the group consisting of Mn, Co, Ni, Cu, Ru, Pd, Ag, Cd, Pt, Au, Rh and Hg, and
w, x, y, and z are leaving groups.

3. The method of claim 1, wherein the complex binds to at least two of the histidine residues in the N-terminal loop.

4. The method of claim 1, wherein the complex binds to at least three of the histidine residues in the N-terminal loop.

5. The method of claim 1, wherein the complex binds to at least one additional amino acid in the N-terminal loop, selected from the group consisting of Asp7, Tyr10 and Glu11.

6. The method of claim 1, wherein the complex is able to penetrate the blood-brain barrier.

7. The method of claim 1, wherein the complex comprises or is conjugated to a targeting moiety selected from the group consisting of polypeptides, nucleic acids, carbohydrates, lipids, β-amyloid ligands, antibodies and dyes.

8. The method of claim 7, wherein the targeting moiety has a hydrophobic region which interacts with the tail of the β-amyloid peptide.

9. The method of claim 8, wherein the targeting moiety targets the complex to a site defined by residues 15 to 21 of the β-amyloid peptide.

10. The method of claim 1, wherein the metal in the complex is Pt.

11. A method for the treatment of Alzheimer's disease in a subject in need of such treatment which comprises administering to said subject a therapeutically effective amount of a metal complex of a 1,10-phenanthroline said metal being Mn, Co, Ni, Cu, Ru, Pd, Ag, Cd, Pt, Au, Rh or Hg.

12. The method of claim 11, wherein the metal complex has the formula

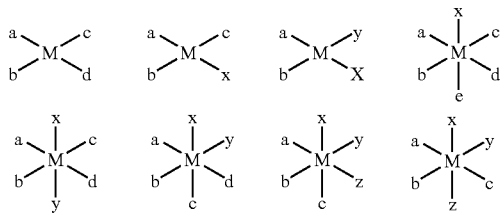

-continued

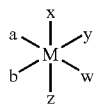

wherein a, b, d, c, and e are chelating non-leaving groups present in said 1,10-phenanthroline, M is a metal selected from the group consisting of Mn, Co, Ni, Cu, Ru, Pd, Ag, Cd, Pt, Au, Rh and Hg, and w, x, y, and z are leaving groups.

13. The method of claim 12, wherein the complex is able to penetrate the blood-brain barrier.

14. The method of claim 2 wherein the complex comprises or is conjugated to a targeting moiety selected from the group consisting of polypeptides, nucleic acid, carbohydrates, lipids, β-amyloid ligands, antibodies and dyes.

15. The method of claim 14, wherein the targeting moiety has a hydrophobic region which interacts with the tail of the β-amyloid peptide.

16. The method of claim 11 wherein the complex comprises or is conjugated to a targeting moiety selected from the group consisting of polypeptides, nucleic acid, carbohydrates, lipids, β-amyloid ligands, antibodies and dyes.

17. The method of claim 16, wherein the targeting moiety has a hydrophobic region which interacts with the tail of the β-amyloid peptide.

18. The method of claim 12 wherein the complex comprises or is conjugated to a targeting moiety selected from the group consisting of polypeptides, nucleic acid, carbohydrates, lipids, β-amyloid ligands, antibodies and dyes.

19. The method of claim 18, wherein the targeting moiety has a hydrophobic region which interacts with the tail of the β-amyloid peptide.

* * * * *